(12) United States Patent
Frijters et al.

(10) Patent No.: US 11,603,538 B2
(45) Date of Patent: Mar. 14, 2023

(54) *PERONOSPORA* RESISTANCE IN *SPINACIA OLERACEA*

(71) Applicant: RIJK ZWAAN ZAADTEELT EN ZAADHANDEL B.V., De Lier (NL)

(72) Inventors: Raoul Jacobus Johannes Maria Frijters, De Lier (NL); Vincent Laurens Adrianus Kock, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 103 days.

(21) Appl. No.: 16/722,582

(22) Filed: Dec. 20, 2019

(65) Prior Publication Data

US 2020/0199615 A1 Jun. 25, 2020

Related U.S. Application Data

(63) Continuation-in-part of application No. PCT/EP2018/086763, filed on Dec. 21, 2018.

(51) Int. Cl.
*C12N 15/82* (2006.01)
*A01H 5/12* (2018.01)
*C12Q 1/6895* (2018.01)

(52) U.S. Cl.
CPC .......... *C12N 15/8282* (2013.01); *A01H 5/12* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 8,742,206 B2 * | 6/2014 | Den Braber et al. | A01H 6/028 426/392 |
| 9,121,029 B2 | 9/2015 | Van Damme et al. | |
| 9,265,275 B2 | 2/2016 | Den Braber | |
| 9,402,363 B1 | 8/2016 | Feitsma | |
| 10,017,781 B2 | 7/2018 | Torjek et al. | |
| 2005/0183150 A1 | 8/2005 | Torisky et al. | |
| 2007/0204368 A1 | 8/2007 | Dale | |
| 2009/0300786 A1 * | 12/2009 | Baerends | A01H 6/028 800/278 |
| 2009/0300788 A1 | 12/2009 | Baerends | |
| 2010/0031385 A1 | 2/2010 | Baerends | |
| 2012/0054894 A1 | 3/2012 | Den Braber | |
| 2013/0055422 A1 | 2/2013 | Baerends | |
| 2013/0055454 A1 | 2/2013 | Den Braber | |
| 2013/0230635 A1 * | 9/2013 | Den Braber | C12N 15/8282 435/410 |
| 2014/0065287 A1 | 3/2014 | Den Braber | |
| 2014/0068799 A1 | 3/2014 | Den Braber | |
| 2014/0068801 A1 | 3/2014 | Den Braber | |
| 2014/0068804 A1 | 3/2014 | Den Braber | |
| 2014/0068805 A1 | 3/2014 | Den Braber | |
| 2014/0068806 A1 | 3/2014 | Den Braber | |
| 2015/0082483 A1 * | 3/2015 | Dijkstra | A01H 1/04 800/301 |
| 2015/0101073 A1 | 4/2015 | Brugmans et al. | |
| 2015/0240256 A1 | 8/2015 | Brugmans et al. | |
| 2016/0152999 A1 | 6/2016 | Torjek et al. | |
| 2016/0177330 A1 * | 6/2016 | Dijkstra | A01H 5/12 800/301 |
| 2017/0027126 A1 | 2/2017 | Dijkstra et al. | |
| 2017/0027127 A1 | 2/2017 | Dijkstra et al. | |
| 2017/0127641 A1 | 5/2017 | De Visser | |
| 2017/0127642 A1 | 5/2017 | De Visser | |
| 2017/0327839 A1 | 11/2017 | Feitsma | |
| 2018/0042198 A1 | 2/2018 | Feitsma | |
| 2019/0127753 A1 | 5/2019 | Kock | |
| 2019/0241905 A1 * | 8/2019 | Kock et al. | A01H 6/028 |

FOREIGN PATENT DOCUMENTS

| | | |
|---|---|---|
| DE | 10 2013 010026 A1 | 12/2014 |
| EP | 2 848 114 A1 | 3/2015 |
| EP | 2 912 940 A1 | 9/2015 |
| WO | 2007/051483 A1 | 5/2007 |
| WO | 2013/064436 A1 | 5/2013 |
| WO | 2015/036378 A1 | 3/2015 |
| WO | 2015/036469 A1 | 3/2015 |
| WO | W02015/036378 * | 3/2015 |
| WO | 2015/171603 A1 | 11/2015 |

(Continued)

OTHER PUBLICATIONS

Irish et al. (2008) Phytopath 90(8):894-900.*
Correll et al. (2011) Eur J Plant Pathol 129:193-205.*
Irish et al. (2007) Plant Dis 91 :1392-96.*
Gou et al. BMC Genomics (2010) 11:19.*
McHale et al. (2006) Genome Biol 7:212.*
Guo et al. (2004) Proc Natl Acad Sci USA 101:9205-10.*
Dodds et al. (2006) Proc Natl Acad Sci USA 103(23):8888-93.*
2011 APS-IPPC Joint Meeting Abstracts of Presentations, Phytopathology (2011) 101(6) Supplemental, S1, S52.

(Continued)

*Primary Examiner* — Russell T Boggs

(74) *Attorney, Agent, or Firm* — Duane Morris LLP; Thomas J. Kowalski; Deborah L. Lu

(57) ABSTRACT

The present invention relates to an allele designated alpha-WOLF 25 which confers resistance to at least one *Peronospora farinosa* f. sp. *spinacea* race, wherein the protein encoded by said allele is a CC-NB S-LRR protein that comprises in its amino acid sequence: a) the motif "MAEI-GYSVC" at its N-terminus; and b) the motif "KWMCLR"; and wherein the LRR domain of the protein has in order of increased preference at least 95%, 96%, 97%, 98%, 99%, 100% sequence similarity to SEQ ID NO: 5. The allele when present in a spinach plant confers complete resistance to at least *Peronospora farinosa* f sp. *spinacea* race Pfs:8, Pfs15 and Pfs:16, and does not confer resistance to Pfs:3.

27 Claims, No Drawings
Specification includes a Sequence Listing.

(56) References Cited

FOREIGN PATENT DOCUMENTS

WO     2018/059653 A1        4/2018
WO     WO2018/060474    *    5/2018

OTHER PUBLICATIONS

Adam Bentham, et al., Animal NLRs Provide Structural Insights into Plant NLF Function, Annals of Botany (2017) 119:689-702.
Joydeep Chakraborty, et al., Functional Diversification of Structurally Alike NLR Proteins in Plants, Plant Science (2018) 269:85-93.
J.C. Correll, et al., Spinach: Better Management of Downy Mildew and White Rust Through Genomics, Eur. J. Plant Pathology (Dec. 4, 2010) 129:193-205.
Peter N. Dodds, et al., Six Amino Acid Changes Confined to the Leucine-Rich Repeat β-Strand/β-Turn Motif Determine the Difference between the P and P2 Rust Resistance Specificities in Flax, The Plant Cell (Jan. 2001) vol. 13, p. 163-178.
Timothy K. Eitas, et al., NB-LRR Proteins: Pairs, Pieces, Perception, Partners, and Pathways, Current Opinion in Plant Biology (2010) 13:472-477.
Feng, et al., Identification of New Races and Deviating Strains of the Spinach Downy Mildew Pathogen *Peronospora farinosa* f. sp. *spinaciae*, Plant Disease (Jan. 2014) 98(1):145-152.
Feng Chunda, et al., Construction of a Spinach Bacterial Artificial Chromosome (BAC) Library as a Resource for Gene Identification and Marker Development, Plant Mol Biol Rep (2015) 33:1996-2005.
GenBank Accession No. XP_021842255 (Aug. 1, 2017).
Haiwei H. Guo, et al., Protein Tolerance to Random Amino Acid Change, PNAS (Jun. 22. 2004) vol. 101, No. 25. p. 9205-9210.
Charlotte Hallavant, et al., The First Archaeobotanical Evidence of *Spinacia oleracea* L. (Spinach) in Late 12th-mid 13th Century A.D. France, French National Centre for Scientific Research, Article: Vegetation History and Archaeobotany, Published online May 21, 2013.
B. M. Irish, et al., Three New Races of the Spinach Downy Mildew Pathogen Identified by a Modified Set of Spinach Differentials, Plant Disease (Nov. 2007) vol. 91, No. 11, p. 1392-1396.
B. M. Irish, et al., Characterization of a Resistance Locus (Pfs-1) to the Spinach Downy Mildew Pathogen (*Peronospora farinosa* f. sp. *spinaciae*) and Development of a Molecular Marker Linked to Pfs-1, Pathology, American Phytopathological Society, US (2008) vol. 98, No. 8, p. 894-900.
Merriam Webster Definition of "as" Sep. 27, 2016.
Simona Proietti, et al., Increase of Ascorbic Acid Content and Nutritional Quality in Spinach Leaves During Physiological Acclimation to Low Temperature, Plant Physiology and Biochemistry (2009) vol. 47, p. 717-723.
Dong Qi, et al., Recent Advances in Plant NLR Structure, Function, Localization, and Signaling, Frontiers in Immunology (2013) vol. 4, Article 348, p. 1-10.
Hongbing She, et al., Fine Mapping and Candidate Gene Screening of the Downy Mildew Resistance Gene RPF1 in Spinach, Theoretical and Applied Genetics (2018) 131:2529-2541.
Octavina C.A. Sukarta, et al., Structure-Informed Insights for NLR Functioning in Plant Immunity, Seminars in Cell & Developmental Biology (2016) 56:134-149.
Yanming Yang, et al., Transgenic Spinach Plants Expressing the Coat Protein of Cucumber Mosaic Virus. In Vitro Cell Dev. Biol.-Plant (1997) 33:200-204.

* cited by examiner

PERONOSPORA RESISTANCE IN SPINACIA OLERACEA

RELATED APPLICATIONS AND INCORPORATION BY REFERENCE

This application is a continuation-in-part application of international patent application Serial No. PCT/EP2018/086763 filed Dec. 21, 2018.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing, which has been submitted electronically and is hereby incorporated by reference in its entirety. Said ASCII copy, is named 00459SL.txt and is 28.6 kb in size.

FIELD OF THE INVENTION

The invention relates to a gene capable of conferring resistance to a spinach plant against one or more *Peronospora farinosa* f. sp. *spinaciae* races. The invention also relates to a spinach plant, to propagation material of said spinach plant, to a cell of said spinach plant, and to seed of said spinach plant carrying the gene. The invention further relates to a method of producing a spinach plant carrying the gene and to the use of the gene in breeding to confer resistance against *Peronospora farinosa* f. sp. *spinaciae*.

BACKGROUND OF THE INVENTION

Downy mildew (*Peronospora farinosa* f sp. *spinaciae*) is a major threat for spinach growers because it directly affects the harvested leaves. In spinach, downy mildew is caused by the oomycete *Peronospora farinosa* f sp. *spinaciae* (formerly known as *P. effusa*). Infection makes the leaves unsuitable for sale and consumption, as it manifests itself phenotypically as yellow lesions on the older leaves, and on the abaxial leaf surface a greyish fungal growth can be observed. The infection can spread very rapidly, and it can occur both in glasshouse cultivation and in soil cultivation. The optimal temperature for formation and germination of *P. farinosa* f. sp. *spinaciae* spores is 9 to 12° C., and it is facilitated by a high relative humidity. When spores are deposited on a humid leaf surface they can readily germinate and infect the leaf. Fungal growth is optimal between 8 and 20° C. and a relative humidity of >80%, and within 6 and 13 days after infection mycelium growth can be observed. Oospores of *P. farinosa* can survive in the soil for up to 3 years, or as mycelium in seeds or living plants.

To date 17 pathogenic races of spinach downy mildew (Pfs) have been officially identified and characterized, and many new candidates are observed in the field. The 17 officially recognized races of *Peronospora farinosa* f sp. *spinaciae*, are designated Pfs:1 to Pfs:17 (Irish et al. Phtypathol. Vol. 98 pg. 894-900, 2008; Plantum NL (Dutch association for breeding, tissue culture, production and trade of seed and young plants) press release, "Benoeming van Pfs: 14, een nieuwe fysio van valse meeldauw in spinazie", Sep. 19, 2012; Report Jim Correl (Univ. Arkansas) and Steven Koike (UC Cooperative Extension, Monterey County), "Race Pfs: 14—Another new race of the spinach downy mildew pathogen", Sep. 18, 2012; Plantum NL press release, "Denomination of Pfs: 15, a new race of downy mildew in spinach", Sep. 2, 2014; Plantum NL press release, "Denomination of Pfs: 16, a new race of downy mildew in spinach, Mar. 15, 2016; Plantum NL press release, Denomination of Pfs: 17, a new race of downy mildew in spinach", Apr. 16, 2018). Races 4 to 16 were identified between 1990 and 2014, while only recently two new *Peronospora* isolates have been identified, termed UA201519B and US1602, which subsequently have been officially named Pfs:16 and Pfs:17 by the International Working Group on *Peronospora* (IWGP) (Plantum NL (Dutch association for breeding, tissue culture, production and trade of seed and young plants) press release, "Denomination of Pfs:16, a new race of downy mildew in spinach", Mar. 15, 2016; Plantum NL press release, Denomination of Pfs:17, a new race of downy mildew in spinach", Apr. 16, 2018. All 17 officially recognized Pfs races are publicly available from the Department of Plant Pathology, University of Arkansas, Fayetteville, Ark. 72701, USA, and also from NAK Tuinbouw, Sotaweg 22, 2371 GD Roelofarendsveen, the Netherlands.

Especially the latest identified *Peronospora* races can break the resistance of many spinach varieties that are currently used commercially worldwide, and they thus pose a serious threat to the productivity of the spinach industry. Therefore, it is crucial to stay at the forefront of developments in this field, as *Peronospora* continuously develops the ability to break the resistances that are present in commercial spinach varieties. For this reason new resistance genes against downy mildew are very valuable assets, and they form an important research focus in breeding and particular in spinach and lettuce breeding. One of the main goals of spinach breeders is to rapidly develop spinach varieties with a resistance to as many *Peronospora* races as possible, including the latest identified races, before these races become wide-spread and pose a threat to the industry.

In commercial spinach varieties resistance against downy mildew is usually caused by so-called R-genes. R-gene mediated resistance is based on the ability of a plant to recognize the invading pathogen. In many cases this recognition occurs after the pathogen has established the first phases of interaction and transferred a so called pathogenicity (or avirulence) factor into the plant cell. These pathogenicity factors interact with host components in order to establish conditions which are favorable for the pathogen to invade the host and thereby cause disease. When a plant is able to recognize the events triggered by the pathogenicity factors a resistance response can be initiated. In many different plant pathogen interaction systems such as the interaction of spinach with different downy mildew strains, the plant initiates these events only after specific recognition of the invading pathogen.

Co-evolution of plant and pathogen has led to an arms race in which a R-gene mediated resistance is sometimes overcome as a consequence of the capability of the pathogen to interact with and modify alternative host targets or the same targets in a different way, such that the recognition is lost and infection can be established successfully resulting in disease. In order to re-establish resistance in a plant, a new R-gene has to be introduced which is able to recognize the mode of action of an alternative pathogenicity factor.

Despite the fact that the durability of R-genes is relatively low, R-genes are in spinach still the predominant form of defense against downy mildew. This is mainly due to the fact that it is the only form of defense that gives absolute resistance. So far plant breeders have been very successful in generating downy mildew resistant spinach varieties by making use of resistance genes residing in the wild germplasm of the crop species. Even though R-genes are extensively used in spinach breeding, until now not much is known of these R-genes.

Only recently it was discovered that the R-genes officially recognized in spinach are in fact all different alleles of the two tightly linked genes, the alpha- and the beta-WOLF genes. This was also the first time that R-genes, or better R-alleles were for the first time characterized at the molecular level, i.e. their nucleotide and amino acid sequence was determined. Although this provides the breeder with tools that increase the efficiency of detecting and selecting R-alleles, adequately responding to newly emerging downy mildew races is still crucial for developing commercially successful spinach varieties.

Citation or identification of any document in this application is not an admission that such document is available as prior art to the present invention.

SUMMARY OF THE INVENTION

Therefore, it is the object of the invention to provide a new resistance allele conferring resistance to a newly emerged downy mildew isolate and to provide molecular biological tools for identifying this new resistance allele.

In the research leading to the present invention, a new allelic variant of the Alpha-WOLF gene as described in WO2018059651 was found. The alpha-WOLF gene encodes a protein that belongs to the CC-NB S-LRR family (Coiled Coil—Nucleotide Binding Site—Leucine-Rich Repeat). Depending on the allelic variant (or the allelic variants) that is (are) present in a spinach plant, said plant will produce a variant of the WOLF protein that confers a certain resistance profile to pathogenic races of *Peronospora farinosa* f. sp. *spinaciae*.

In the context of this invention the term "allele" or "allelic variant" is used to designate a version of the gene that is linked to a specific phenotype, i.e. resistance profile. It was found that a spinach plant may carry one or two WOLF genes. Each of these two WOLF genes encompasses multiple alleles, each allele conferring a particular resistance profile. In the context of this invention an allele or allelic variant is a nucleic acid.

The beta WOLF gene is located on scaffold12735 (sequence: GenBank: KQ143339.1), at position 213573-221884. In case the spinach plant also carries or only carries the alpha-WOLF gene, the alpha-WOLF gene is located at approximately the same location as where the beta-WOLF gene is located on scaffold12735 in the Viroflay genome assembly.

The newly found alpha-WOLF allele provides at least resistance to downy mildew race Pfs:16. Alpha-WOLF 25 also provides resistance to Pfs:8 and Pfs:15.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of a plant with the alpha-WOLF 25 allele of the invention in its genome were deposited with NCIMB Ltd, Ferguson Building, Craibstone Estate, Bucksburn, Aberdeen AB21 9YA, UK, on 2 Oct. 2019, under deposit accession number NCIMB 43495. The Deposits with NCIMB Ltd, under deposit accession number 43495 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

A genome assembly for spinach variety Viroflay—which is susceptible to all known pathogenic races of *Peronospora farinosa* f. sp. *spinaciae*—is publicly available (*Spinacia oleracea* cultivar SynViroflay, whole genome shotgun sequencing project; Bioproject: PRJNA41497; GenBank: AYZV00000000.2; BioSample: SAMN02182572, see also Dohm et al, 2014, Nature 505: 546-549). In this genome assembly for Viroflay, the beta-WOLF gene is located on scaffold12735 (sequence: GenBank: KQ143339.1), at position 213573-221884. The sequence covered by this interval comprises the entire genomic sequence of the beta-WOLF gene of Viroflay, plus 2000 basepairs sequence upstream from the gene, plus the sequence downstream from the gene, up to the locus of the neighbouring gene that is situated downstream from the WOLF gene. Spinach variety Viroflay only possesses a single WOLF gene, namely a beta-WOLF gene, but most other spinach lines harbor a single alpha-type WOLF gene at the same location in the genome. Other spinach lines harbor two WOLF genes at approximately the same location in the genome. In such cases, the two WOLF genes are positioned adjacent to each other. In most spinach lines that harbor two WOLF genes, one of said WOLF genes belongs to the alpha-type, and the other WOLF gene belongs to the beta-type. It was observed that this allelic variation in the WOLF locus is responsible for differences in resistance to pathogenic races of *Peronospora farinosa* f. sp. *spinaciae*.

The difference between an allele of an alpha-WOLF gene and an allele of a beta-WOLF gene lies in the presence of specific conserved amino acid motifs in the encoded protein sequence. As mentioned above, all WOLF proteins possess—from N- to C-terminus—the following domains that are generally known in the art: a coiled coil domain (RX-CC-like, cd14798), an NBS domain (also referred to as "NB-ARC domain", pfam00931; van der Biezen & Jones, 1998, Curr. Biol. 8: R226-R228), and leucine-rich repeats (IPR032675) which encompass the LRR domain. In addition, all WOLF proteins comprise in their amino acid sequence the motif "MAEIGYSVC" (SEQ ID NO: 10) at the N-terminus. In addition to this, all alpha-WOLF proteins comprise the motif "KWMCLR" (SEQ ID NO: 11) in their amino acid sequence, whereas all beta-WOLF proteins comprise the motif "HVGCVVDR" (SEQ ID NO: 15) in their amino acid sequence.

The present invention relates to a new *Peronospora farinosa* f. sp. *spinaciae* resistance conferring allele of the alpha-WOLF gene designated alpha-WOLF 25.

In particular, the invention relates to a *Peronospora farinosa* f sp. *spinaciae* resistance conferring allele designated alpha-WOLF 25 wherein the protein encoded by said allele is a CC-NBS-LRR protein that comprises in its amino acid sequence: a) the motif "MAEIGYSVC" (SEQ ID NO: 10) at its N-terminus; and b) the motif "KWMCLR" (SEQ ID NO: 11); and wherein the LRR domain of the protein has in order of increased preference at least 95%, 96%, 97%, 98%, 99%, 100% sequence similarity to SEQ ID NO: 5. Optionally, the alpha-WOLF 25 allele further comprise an additional motif in their amino acid sequence, namely "DQEDEGEDN" (SEQ ID NO: 12).

The invention further relates to a *Peronospora farinosa* f. sp. *spinaciae* resistance conferring allele designated alpha-WOLF 25 wherein the protein encoded by said allele is a CC-NBS-LRR protein that comprises in its amino acid sequence: a) the motif "MAEIGYSVC" (SEQ ID NO: 10) at its N-terminus; and b) the motif "KWMCLR" (SEQ ID NO: 11); and wherein the LRR domain of the protein has in order of increased preference at least 93%, 94%, 95%, 96%, 97%, 98%, 99%, 100% sequence identity to SEQ ID NO: 5. Optionally, the alpha-WOLF 25 allele further comprise an additional motif in their amino acid sequence, namely "DQEDEGEDN" (SEQ ID NO: 12).

The invention also relates to an alpha-WOLF 25 allele having an LRR domain which has a genomic sequence that in order in order of increased preference has at least 93%, 94%, 95%, 96%, 97%, 98%, 99%, 100% sequence similarity to SEQ ID NO: 4.

The invention also relates to an alpha-WOLF 25 allele having an LRR domain which has a genomic sequence that in order of increased preference has at least 96%, 97%, 98%, 99%, 100% sequence identity to SEQ ID NO: 4.

For the purpose of this invention, the LRR domain of the protein of the alpha-WOLF 25 allele is defined as the amino acid sequence that in order of increased preference has at least 95%, 96%, 97%, 98%, 99%, 100% sequence similarity to SEQ ID NO: 5.

For the purpose of this invention, the LRR domain of the protein of the alpha-WOLF 25 allele is defined as the amino acid sequence that in order of increased preference has at least 93%, 94%, 95%, 96%, 97%, 98%, 99%, 100% sequence identity to SEQ ID NO: 5.

The skilled person is familiar with methods for the calculation of sequence similarity and sequence identity. Sequence similarity for an amino acid sequence is calculated using EMBOSS stretcher 6.6.0 (www.ebi.ac.uk/Tools/psa/emboss stretcher), using the EBLOSUM62 matrix with settings Gap open: 12 and Gap extend: 2. In case of DNA, sequence similarity is calculated using the DNA full matrix with settings Gap open:16 and Gap extend: 4.

The LRR domain of the alpha-WOLF 25 allele as defined herein can be determined by amplifying and sequencing the genomic DNA encoding for the amino acid sequence of LRR domain using specific primers, and subsequently translating the DNA sequence into an amino acid sequence, thereby applying common sense in choosing the correct reading frame. The skilled person is capable of doing this, using freely available online bioinformatics tools such as can be found here: expasy.org/translate/.

The genomic sequence of a LRR domain of an alpha-WOLF gene such as alpha-WOLF 25 can be amplified using a primer pair having a forward primer which is a nucleic acid molecule having the sequence of SEQ ID NO: 1 and a reverse primer which is a nucleic acid molecule having the sequence of SEQ ID NO: 2.

The invention also relates to a nucleic acid molecule which confers resistance to at least one *Peronospora farinosa* f sp. *spinacea* race, wherein the protein encoded by said nucleic acid molecule is a CC-NBS-LRR protein that comprises in its amino acid sequence: a) the motif "MAEIGYSVC" (SEQ ID NO: 10) at its N-terminus; and b) the motif "KWMCLR" (SEQ ID NO: 11); and wherein the LRR domain of the protein has in order of increased preference at least 95%, 96%, 97%, 98%, 99%, 100% sequence similarity to SEQ ID NO: 5. Optionally this nucleic acid molecule is an isolated nucleic acid molecule.

The invention also relates to a nucleic acid molecule which confers resistance to at least one *Peronospora farinosa* f sp. *spinacea* race, wherein the protein encoded by said nucleic acid molecule is a CC-NBS-LRR protein that comprises in its amino acid sequence: a) the motif "MAEIGYSVC" (SEQ ID NO: 10) at its N-terminus; and b) the motif "KWMCLR" (SEQ ID NO: 11); and wherein the LRR domain of the protein has in order of increased preference at least 93%, 94%, 95%, 96%, 97%, 98%, 99%, 100% sequence identity to SEQ ID NO: 5. Optionally this nucleic acid molecule is an isolated nucleic acid molecule.

The allele shows a segregation pattern that is consistent with that of a dominant inheritance for the resistance it confers to downy mildew races Pfs:8, Pfs:15 and Pfs:16.

PCR conditions for amplifying the LRR domain-encoding region of an alpha-WOLF gene using primers having SEQ ID NO: 1 and SEQ ID NO: 2 are, using Platinum Taq enzyme (Thermo Fisher Scientific): 3 minutes at 95° C. (initial denaturing step); 40 amplification cycles, each cycle consisting of: 30 seconds denaturation at 95° C., 30 seconds annealing at 60° C., and 30 seconds extension at 72° C.; 2 minutes at 72° C. (final extension step).

The LRR domain of a beta-WOLF gene, e.g. the null allele as present in variety Viroflay, can be amplified using a forward primer which is a nucleic acid molecule having the sequence of SEQ ID NO: 3 and a reverse primer which is a nucleic acid molecule having the sequence of SEQ ID NO: 2.

PCR conditions for amplifying the LRR domain-encoding region of a beta-WOLF gene using primers having SEQ ID NO: 2 and SEQ ID NO: 3 are as follows, using Platinum Taq enzyme (Thermo Fisher Scientific):—3 minutes at 95° C. (initial denaturing step); 40 amplification cycles, each cycle consisting of: 30 seconds denaturation at 95° C., 50 seconds annealing at 58° C. and 50 seconds extension at 72° C.; 2 minutes at 72° C. (final extension step).

Therefore, the invention also relates to a primer pair for amplifying the LRR domain of an alpha-WOLF gene, more in particular for amplifying the LRR domain of an alpha-WOLF 25 allele wherein the forward primer is a nucleic acid molecule having the sequence of SEQ ID NO: 1 and the reverse primer which is a nucleic acid molecule having the sequence of SEQ ID NO: 2. The primers disclosed herein have been specifically designed for selectively amplifying part of a WOLF gene, and not of any other CC-NB S-LRR protein-encoding genes.

The invention relates to an alpha-WOLF 25 allele which has a coding sequence that in order of increased preference has at least 80%, 81%, 82%, 83%, 84%,85%, 86%, 87%, 88%, 89%, 90%, 91%, 92%, 93%, 94%, 95%, 96%, 97%, 98%, 99%, 100% sequence similarity to SEQ ID NO: 8.

The invention also relates to an alpha-WOLF 25 allele which has a coding sequence that in order of increased preference has at least 80%, 81%, 82%, 83%, 84%,85%, 86%, 87%, 88%, 89%, 90%, 91%, 92%, 93%, 94%, 95%, 96%, 97%, 98%, 99%, 100% sequence identity to SEQ ID NO: 8.

In a further aspect of the invention the alpha-WOLF 25 allele encodes for a protein having an amino acid sequence which in order of increased preference has at least 92%, 93%, 94%, 95%, 96%, 97%, 98%, 99%, 100% sequence similarity to SEQ ID NO: 9.

In a further aspect of the invention the alpha-WOLF 25 allele encodes for a protein having an amino acid sequence which in order of increased preference has at least 92%, 93%, 94%, 95%, 96%, 97%, 98%, 99%, 100% sequence identity to SEQ ID NO: 9.

The alpha-WOLF 25 allele when present in a spinach plant confers complete resistance to at least one of the 17 officially recognized Peronospora farinosa f sp. spinacea races. In a further embodiment, the alpha-WOLF 25 allele when present in a spinach plant confers complete resistance to at least two of the 17 officially recognized Peronospora farinosa f. sp. spinacea races. In a further embodiment, the alpha-WOLF 25 allele when present in a spinach plant confers complete resistance in order of increased preference to at least two, three, four, five, six, seven, eight, nine, ten, eleven, twelve, thirteen, fourteen, fifteen, sixteen or all of the seventeen officially recognized Peronospora farinosa f. sp. spinacea races.

The alpha-WOLF 25 allele when heterozygously or homozygously present in a spinach plant confers at least complete resistance to the officially recognized Peronospora farinosa f. sp. spinacea races Pfs:8, Pfs:15 and Pfs:16, and does not confer resistance to downy mildew race Pfs:3 (see Table 1).

The resistance of a spinach plant against one or more races of Peronospora farinosa f sp. spinaciae can be determined using a seedling test. Herein, a seedling test is defined as a test wherein spinach plants are planted in trays containing growth medium, optionally fertilized twice a week after seedling emergence. Plants were inoculated at the first true leaf stage with a sporangial suspension having a concentration of approximately $2.5\times10^5$/ml of one of the pathogenic races of Peronospora farinosa f sp. spinaciae or isolates to be tested. The inoculated plants are placed in a dew chamber at 18° C. with 100% relative humidity for a 24 h period, and then moved to a growth chamber at 18° C. with a 12 h photoperiod for 6 days. After 6 days, the plants are returned to the dew chamber for 24 h to induce sporulation, and subsequently scored for a disease reaction. Preferably, 30 plants per race are tested.

As used herein, a plant is completely resistant against a Peronospora farinosa f. sp. spinaciae race when a plant shows no symptoms in the seedling test described herein.

As used herein, a plant is intermediately resistant against a Peronospora farinosa f. sp. spinaciae race when a plant shows only symptoms of chlorosis, or sporulation occurring only on the tips of the cotyledons in the seedling test described herein.

As used herein, a plant is susceptible to an isolate of a Peronospora farinosa f. sp. spinaciae race when a plant shows more than only symptoms of chlorosis, or when sporulation occurs on area larger than only the tips of the cotyledons in the seedling test described herein.

Another aspect of the invention relates to a spinach plant, comprising the alpha-WOLF 25 allele of invention, of which a representative sample of seed was deposited with the NCIMB under NCIMB accession number 43495.

In a further embodiment the plant of the invention which comprises the alpha-WOLF 25 allele is an agronomically elite spinach plant. In the context of this invention an agronomically elite spinach plant is a plant having a genotype that results into an accumulation of distinguishable and desirable agronomic traits which allow a producer to harvest a product of commercial significance, preferably the agronomically elite spinach plant comprising the alpha-WOLF 25 allele is a plant of an inbred line or a hybrid.

As used herein, a plant of an inbred line is a plant of a population of plants that is the result of three or more rounds of selfing, or backcrossing; or which plant is a double haploid. An inbred line may e.g. be a parent line used for the production of a commercial hybrid.

As used herein, a hybrid plant is a plant which is the result of a cross between two different plants having different genotypes. More in particular, a hybrid plant is the result of a cross between plants of two different inbred lines, such a hybrid plant may e.g. be a plant of an $F_1$ hybrid variety.

A plant carrying the alpha-WOLF 25 allele in heterozygous form may further comprise a beta-WOLF 0 allele as e.g. present in variety Viroflay wherein the beta-WOLF 0 allele does not confer any resistance to downy mildew. However, a plant heterozygous for the alpha-WOLF 25 allele may further comprise an allele of the alpha/beta-WOLF gene that does provide resistance to downy mildew. Preferably, such an allele would complement the alpha-WOLF 25 allele such that the spinach plant will be at least intermediately resistant to one or more other races to which the alpha-WOLF 25 allele does not provide resistance. Most preferably the other allele of the alpha/beta-WOLF gene complements the alpha-WOLF 25 allele such that the plant is resistant to Peronospora farinosa f. sp. spinaciae races Pfs:1 to Pfs:17. In one embodiment such a plant is an agronomically elite plant.

Alternatively, the resistance profile of a plant carrying the alpha-WOLF 25allele is complemented by a resistance conferring allele of a totally different gene. Examples of such genes are e.g. DMR1 as described in U.S. Pat. No.

8,354,570, DMR6 as described in U.S. Pat. No. 9,121,029 and p10 as described in US20170327839.

The invention thus relates to a spinach plant carrying the alpha-WOLF 25 allele and further comprising a genetic determinant resulting in resistance against *Peronospora farinosa* f sp. *spinacea* races Pfs:1 to Pfs:17. The genetic determinant can be another resistance conferring alpha/beta-WOLF allele or a resistance conferring allele of a totally different gene.

The invention further relates to propagation material comprising the alpha-WOLF 25 allele. In one embodiment, the propagation material is suitable for sexual reproduction. Such propagation material comprises for example a microspore, pollen, ovary, ovule, embryo sac and egg cell. In another embodiment, the propagation material is suitable for vegetative reproduction. Such propagation material comprises for example a cutting, root, stem, cell, protoplast, and a tissue culture of regenerable cells. A part of the plant that is suitable for preparing tissue cultures is in particular a leaf, pollen, an embryo, a cotyledon, a hypocotyl, a meristematic cell, a root tip, an anther, a flower, a seed and a stem.

The invention furthermore relates to a cell of a spinach plant comprising the alpha-WOLF 25 allele. Such a cell may be either in isolated form or may be part of the complete plant or parts thereof and then still constitutes a cell of the invention because such a cell harbors the alpha-WOLF 25 allele that confers resistance to downy mildew. Each cell of a plant of the invention carries the genetic information that confers resistance to *Peronospora farinosa* f sp. *spinaciae*. Such a cell of the invention may also be a regenerable cell that may be used to regenerate a new plant comprising the allele of the invention.

Yet another aspect of the invention relates to a method for making a hybrid spinach seed comprising crossing a first parent spinach plant with a second parent spinach plant and harvesting the resultant hybrid spinach seed, wherein said first and/or second parent spinach plant comprises the alpha-WOLF 25 allele. In particular embodiment, the first and/or second parent plant is a plant of an inbred line as defined herein.

The invention further relates to a hybrid spinach plant grown from seed produced by crossing a first parent spinach plant with a second parent spinach plant and harvesting the resultant hybrid spinach seed, wherein said first and/or second parent spinach plant comprises the alpha-WOLF 25 allele.

Determining the genomic DNA or coding DNA sequence of at least part of a WOLF gene in the genome of a spinach plant may be performed using any suitable molecular biological method known in the art, including but not limited to (genomic) PCR amplification followed by Sanger sequencing, whole-genome-sequencing, transcriptome sequencing, sequence-specific target capture followed by next-generation sequencing (using, for example, the xGen® target capture system of Integrated DNA Technologies), specific amplification of LRR-domain-comprising gene sequences (using, for example, the RenSeq methodology, as described in U.S. patent application Ser. No. 14/627,116, and in Jupe et al., 2013, Plant J. 76: 530-544) followed by sequencing, etcetera.

In one embodiment the invention relates to a method for identifying a plant carrying the alpha-WOLF 25 allele comprises determining the DNA sequence coding for the LRR domain as defined herein.

In a further embodiment of the method the LRR domain of the alpha-WOLF 25 allele is determined by using a primer pair to amplify the genomic DNA region of the LRR domain. The forward primer is preferably a nucleic acid molecule having the sequence of SEQ ID NO: 1 and the reverse primer is preferably a nucleic acid molecule having the sequence of SEQ ID NO: 2.

Another aspect of the invention relates to a method for producing a spinach plant comprising resistance to *Peronospora farinosa* f sp. *spinaciae* comprising: (a) crossing a plant comprising the alpha-WOLF 25 allele, with another plant; (b) optionally performing one or more rounds of selfing and/or crossing; (c) optionally selecting after each round of selfing or crossing for a plant that comprises the alpha-WOLF 25 allele.

Selecting a plant comprising the alpha-WOLF 25 allele can be done genotypically by determining the presence of the genomic DNA sequence of the NBS-LRR domain of the allele having in order of increased preference 95%, 96%, 97%, 98%, 99%, 100% sequence similarity to SEQ ID NO: 4, or 95%, 96%, 97%, 98%, 99%, 100% sequence identity to SEQ ID NO: 4.

In another embodiment, selecting a plant comprising the alpha-WOLF 25 allele can be done genotypically by determining the presence the coding sequence of the entire allele.

Alternatively, the presence of the alpha-WOLF 25 allele can be determined phenotypically by assaying a plant in a disease test, for example the test as described herein.

The invention further relates to the use of a spinach plant carrying the alpha-WOLF 25 allele in breeding to confer resistance against *Peronospora farinosa* f. sp. *spinaciae*.

The invention also relates to a breeding method for the development of spinach plants carrying the alpha-WOLF 25 allele of the invention wherein germplasm which comprises said allele is used. Seed capable of growing into a plant comprising the allele of the invention and being representative for the germplasm was deposited with the NCIMB under deposit number NCIMB 43495.

In another aspect, the invention relates to a method for the production of a spinach plant which comprises alpha-WOLF 25 allele, which method comprises: (a) crossing a plant comprising the allele with another plant; (b) optionally selecting for plants comprising said allele in the F1; (c) optionally backcrossing the resulting F1 with the preferred parent and selecting for plants that have the said allele in the BC1F1; (d) optionally performing one or more additional rounds of selfing, crossing, and/or backcrossing, and subsequently selecting for a plant which comprises the said allele or shows the resistance profile corresponding to said allele. The invention also encompasses a spinach plant produced by this method.

The invention also relates to a harvested leaf of a spinach plant of the invention, to a food product which comprises a harvested leaf of a spinach plant of the invention, either in natural or in processed form.

Spinach leaves are sold in packaged form, including without limitation as pre-packaged spinach leaves or as processed in a salad comprising said leaves. Mention of such a package is e.g. made in U.S. Pat. No. 5,523,136, which provides packaging film, and packages from such packaging film, including such packaging containing leafy produce, and methods for making and using such packaging film and packages, which are suitable for use with the spinach leaves of the invention. Thus, the invention comprehends the use of and methods for making and using the leaves of the spinach plant of the invention, as well as leaves of spinach plants derived from the invention.

The invention further relates to a container which comprises one or more plants of the invention, or one or more spinach plants derived from a plant of the invention, in a growth substrate for harvest of leaves from the plant, in a domestic environment. This way the consumer may pick very fresh leaves for use in salads, when the plant is in a ready-to-harvest condition.

The invention also relates to the use of a spinach plant, of which representative seed was deposited with the NCIMB under accession number NCIMB 43495, in the production of a spinach plant comprising the alpha-WOLF 25 allele.

In a further embodiment the said spinach plant is a hybrid, doubled haploid, or inbred spinach plant.

Another aspect of the invention is the use of a cell comprising the alpha-WOLF 25 allele for the production of a spinach plant showing resistance to *Peronospora farinosa* f sp. *spinaciae*.

The invention also relates to the use of a tissue culture comprising the alpha-WOLF 25 allele for the production of a spinach plant showing resistance to *Peronospora farinosa* f. sp. *spinaciae*.

TABLE 1

Resistance profile conferred by the Alpha-WOLF 25 allele.
Alpha-WOLF 25 resistance profile

| *Peronospora farinosa* f. sp. *spinaciae* race | Resistance score |
| --- | --- |
| Pfs:1 | nt |
| Pfs:2 | nt |
| Pfs:3 | + |
| Pfs:4 | nt |
| Pfs:5 | nt |
| Pfs:6 | nt |
| Pfs:7 | nt |
| Pfs:8 | − |
| Pfs:9 | nt |
| Pfs:10 | nt |
| Pfs:11 | nt |
| Pfs:12 | nt |
| Pfs:13 | nt |
| Pfs:14 | nt |
| Pfs:15 | − |
| Pfs:16 | − |

A "−" means complete resistance against a particular downy mildew race;
"(−)" means intermediate resistance against a particular downy mildew race;
"+" means that the allele confers no resistance and would cause a plant only carrying the Alpha-WOLF 25 allele to be fully susceptible for that particular downy mildew race;
"nt" means that it has not been tested against that isolate.

TABLE 2

Sequence information.

| | |
| --- | --- |
| SEQ ID NO: 1:<br>Forward primer<br>LRR domain (Alpha) | ACAAGTGGATGTGTCTTAGG |
| SEQ ID NO: 2:<br>Reverse primer<br>LRR domain (Alpha) | TTCGCCCTCATCTTCCTGG |
| SEQ ID NO: 3:<br>Forward primer<br>LRR domain (Beta) | TCACGTGGGTTGTGTTGT |
| SEQ ID NO: 4:<br>Amplicon of<br>LRR domain of<br>the alpha-<br>WOLF 25 allele | ACAAGTGGATGTGTCTTAGGATGTTGGACTTGTCAAATTCAG<br>ATGTTAAAAGTTTGCCTAATTCAATAGGTAAGTTGTTGCACT<br>TACGGTATCTTAACCTGTCAAATAATAGAAATCTAAAGATAC<br>TTCCTGATGCAATTACAAGACTGCATAACTTGCAGACACTAC<br>TTTTAGAAGATTGCAGAAGTTTAAAGGAGTTGCCAAAAGAT<br>TTTTGCAAATTGGTCAAACTGAGGCACTTGGATTTAAGGTTT<br>TGTTCTGATTTGATTGGTATGCCATTGGGAATGGATAGGCTA<br>ACTAGTCTTAGAGTACTGCCATTCTTTGTGGTGGGTAGGAAG<br>GAACAAAGTGTTGATGATGAGCTGAAAGCCCTAAAAGGCCT<br>CACCGAGATAAAAGGCTCCATTCGTATTAGAATCCATTCAA<br>AGTATAGAATAGTTGAAGGCATGAATGACACAGGAGGAGCT<br>GGGTATTTGAAGAGCATGAAACATCTCACGAGGGTTATTATT<br>AGATTTGATGATAAAGAAGGTGGATGTGTTAACCCTGAAGC<br>TGTGTTGGCAACCCTAGAGCCACCTTCAAATATCAAGAGCTT<br>ATCTATAGATAATTACGATGGTACAACAATTCCAGTATGGG<br>GAAGAGCAGAGATTAATTGGGCAATCTCCCTCTCACATCTTG<br>TCGACATCCAGCTTTGGTGTTGTAGTAATTTGCAGGAGATGC<br>CAGTGCTGAGTAAACTGCCTCATTTGAAATCACTGTATCTTT<br>TTAAGTTTTGTAAGTTAGAGTACATGGAGAGTAGAAGCAGC<br>AGCAGTAGCAGTGACACAGAAGCAGCAACACCAGAATTACC<br>AACATTCTTCCCTTCCCTTGAAAAACTTACACTTTGGTATCTG<br>GAAAAGTTGAAGGGTTTTGGGAACAGGAGACCGAGTAGTTT<br>TCCCCGCCTCTCTAAATTGGAAATCGGGAATGCCCAGATCT<br>AACGTGGTTTCCTCCTTGTCCAAGCCTTAAAACGTTGAAATT<br>GGAAAAAAACAATGAAGCGTTGCAAATAATAGTAAAAATA<br>ACAACAACAAGAGGTAAAGAAGAAAAAGAAGAAGACAAGA<br>ATGCTGGTGTTGGAAATTCACAAGATGATGACAATGTCAAA<br>TTACGGAAGGTGGAAATAGACAATGTGAGTTATCTCAAATC<br>ACTGCCCACAAATTGTCTTACTCACCTCAAAATAACTGGAAT<br>AGATTACAGGGAGGGGAGATTGAATCAGATTCCGTGGAGG<br>AGGAGATTGAATTGGAAGTTGGGGAGGCATTTCAGAAGTGT |

TABLE 2-continued

Sequence information.

|  |  |
|---|---|
| | GCATCTTCTTTGAGAAGCCTCATCATAATCGGAAATCACGGA<br>ATAAATAAAGTGATGAGACTGTCTGGAAGAACAGGGTTGGA<br>GCATTTCACTCTGTTGGACTCACTCAAACTTTCAAATATAGA<br>AGACCAGGAAGATGAGGGCGAA |
| SEQ ID NO: 5:<br>amino acid<br>sequence<br>encoded by<br>amplicon of<br>LRR domain of<br>alpha-WOLF 25 | KWMCLRMLDLSNSDVKSLPNSIGKLLHLRYLNLSNNRNLKILP<br>DAITRLHNLQTLLLEDCRSLKELPKDFCKLVKLRHLDLRFCSDL<br>IGMPLGMDRLTSLRVLPFFVVGRKEQSVDDELKALKGLTEIKG<br>SIRIRTHSKYRIVEGMNDTGGAGYLKSMKHLTRVIIRFDDKEGG<br>CVNPEAVLATLEPPSNIKSLSIDNYDGTTIPVWGRAEINWAISLS<br>HLVDIQLWCCSNLQEMPVLSKLPHLKSLYLFKFCKLEYMESRS<br>SSSSSDTEAATPELPTFFPSLEKLTLWYLEKLKGFGNRRPSSFPR<br>LSKLEIWECPDLTWFPPCPSLKTLKLEKNNEALQIIVKITTTRGK<br>EEKEEDKNAGVGNSQDDDNVKLRKVEIDNVSYLKSLPTNCLT<br>HLKITGIDYREGEIESDSVEEEIELEVGEAFQKCASSLRSLIIIGNH<br>GINKVIVIRLSGRTGLEHFTLLDSLKLSNIEDQEDEGE |
| SEQ ID NO: 6:<br>Amplicon of<br>LRR domain of<br>the beta-WOLF<br>0 allele | TCACGTGGGTTGTGTTGTCGATAGAGATCCAGAAATAGTCTT<br>TTTATGTAGCAATAAGATTCGTTCGTATATTAGCGGTCGCTG<br>CATAAAGAATCCGGTGGATTCACAAATAGACAACTGGATGT<br>GCCTTAGGGTGTTGGACTGTCAGATTCATGTGTTAAAGATT<br>TGTCTGATTCAATAGGTAAGCTGCTGCACTTAAGGTATCTTA<br>ACCTCTCTTCTAATATAAAGTTGGAGATAATCCCTGATGCAA<br>TTACAAGACTGCATAACTTGCAGACACTACTTTTAGAAGATT<br>GCAGAAGTTTAAAGGAGTTGCCAAAAGATTTTTGCAAATTG<br>GTCAAACTGAGGCACTTGGAATTACAGGGTTGTCATGATTTG<br>ATTGGTATGTCATTTGGAATGGATAAGCTAACTAGTCTTAGA<br>ATACTACCAAACATTGTGGTGGGTAGGAAGGAACAAAGTGT<br>TGATGATGAGCTGAAAGCCCTAAAAGGCCTCACCGAGATAA<br>AAGGCTCCATTGATATCACAATCTATTCAAAATATAGAAGA<br>GTTGAAGGCATGAATGGCACAGGAGGAGGAGCTGGGTATTT<br>GAAGAGCATGAAACATCTCACGGGGGTTAATATTACATTTG<br>ATGAAGGTGGATGTGTTAACCCTGAAGCTGTGTATTTGAAG<br>AGCATGAAACATCTCACGAGGGTTATTATTATATTTGATTAT<br>AAAGGTGGATGTGTTAACCCTGAAGCTGTGTTGGCAACCCT<br>AGAGCCACCTTCAAATATCAAGAGGTTAGAGATGTGGCATT<br>ACAGTGGTACAACAATTCCAGTATGGGGAAGAGCAGAGATT<br>AATTGGGCAATCTCCCTCTCACATCTTGTCGACATCACGCTT<br>GAAGATTGTTACAATTTGCAGGAGATGCCAGTGCTGAGTAA<br>ACTGCCTCATTTGAAATCACTGGAACTTACAGAGTTGGATAA<br>CTTAGAGTACATGGAGAGTAGAAGCAGCAGCAGTAGCAGTG<br>ACACAGAAGCAGCAACACCAGAATTACCAACATTCTTCCCT<br>TCCCTTGAAAAACTTACACTTTGGCGTCTGGACAAGTTGAAG<br>GGTTTTGGGAACAGGAGATCGAGTAGTTTTCCCCGCCTCTCT<br>AAATTGGAAATCTGGAAATGTCCAGATCTAACGTCATTTCCT<br>TCTTGTCCAAGCCTTGAAGAGTTGGAATTGAAAGAAAACAA<br>TGAAGCGTTGCAAATAATAGTAAAAATAACAACAACAAGAG<br>GTAAAGAAGAAAAAGAAGAAGACAAGAATGCTGGTGTTGG<br>AAATTCACAAGATGATGACAATGTCAAATTATGGAAGGTGG<br>AAATAGACAATCTGGGTTATCTCAAATCACTGCCCACAAATT<br>GTCTGACTCACCTCGACCTTACAATAAGTGATTCCAAGGAGG<br>GGGAGGGTGAATGGGAAGTTGGGGATGCATTTCAGAAGTGT<br>GTATCTTCTTTGAGAAGCCTCACCATAATCGGAAATCACGGA<br>ATAAATAAAGTGAAGAGACTGTCTGGAAGAACAGGGTTGGA<br>GCATTTCACTCTGTTGGAATCACTCAAACTTTCAGATATAGA<br>AGACCAGGAAGATGAGGGCGAA |
| SEQ ID NO: 7:<br>amino acid<br>sequence<br>encoded by<br>amplicon of<br>LRR domain<br>Beta Wolf 0<br>(Viroflay) | HVGCVVDRDPEIVFLCSNKIRSYISGRCIKNPVDSQIDNWMCLR<br>VLDLSDSCVKDLSDSIGKLLHLRYLNLSSNIKLEIIPDAITRLHNL<br>QTLLLEDCRSLKELPKDFCKLVKLRHLELQGCHDLIGMSFGMD<br>KLTSLRILPNIVVGRKEQSVDDELKALKGLTEIKGSIDITIYSKYR<br>RVEGMNGTGGGAGYLKSMKHLTGVNITFDEGGCVNPEAVYL<br>KSMKHLTRVIIIFDYKGGCVNPEAVLATLEPPSNIKRLEMWHYS<br>GTTIPVWGRAEINWAISLSHLVDITLEDCYNLQEMPVLSKLPHL<br>KSLELTELDNLEYMESRSSSSSSDTEAATPELPTFFPSLEKLTLW<br>RLDKLKGFGNRRSSSFPRLSKLEIWKCPDLTSFPSCPSLEEELEK<br>ENNEALQIIVKITTTRGKEEKEEDKNAGVGNSQDDDNVKLWK<br>VEIDNLGYLKSLPTNCLTHLDLTISDSKEGEGEWEVGDAFQKC<br>VSSLRSLTIIGNHGINKVKRLSGRTGLEHFTLLESLKLSDIEDQE<br>DEGE |
| SEQ ID NO: 8:<br>coding sequence<br>of the alpha-<br>WOLF 25 allele | ATGGCCGAAATCGGATACTCGGTTTGTGCGAAACTCATCGA<br>AGTGATTGGCAGTGAGCTGATCAAAGAGATTTGTGACACAT<br>GGGGTTACAAATCTCTTCTTGAGGACCTCAACAAAACTGTAT<br>TGACGGTCAGGAACGTTCTCATTCAAGCCGGGGTGATGCGG<br>GAGCTTACTAGTGAACAACAAGGTTTCATTGCAGACCTTAA<br>AGATGTTGTTTATGATGCTGATGACTTGTTCGACAAGTTACT<br>CACTCGTGCTGAGCGAAAACAGATTGATGGAAACGAAATCT |

TABLE 2-continued

Sequence information.

```
CTGAAAAGGTACGTCGTTTCTTTTCCTCTAGTAACAAGATCG
GTCAAGCTTACTACATGTCTCGTAAGGTTAAGGAAATTAAG
AAGCAGTTGGATGAAATTGTTGATAGGCATACAAAATTTGG
GTTTAGTGCTGAGTTTATACCTGTTTGTAGGGAAAGGGGGAA
CGAGAGGGAAACACGTTCATATATAGATGTCAAGAATATTC
TTGGGAGGGATAAAGATAAGAATGATATCATTGATAGGTTG
CTTAATCGTAATGGTAATGAAGCTTGTAGTTTCCTGACCATA
GTGGGAGCGGGAGGATTGGGAAAAACTGCTCTTGCACAACT
TGTGTTCAATGATGAAAGGGTCAAAATTGAGTTTCATGATTT
GAGGTATTGGGTTTGTGTCTCTGATCAAGATGGGGCCAATT
TGATGTGAAAGAAATCCTTTGTAAGATTTTAGAGGTGGTTAC
TAAGGAGAAAGTTGATAATAGTTCCACATTGGAATTGGTGC
AAAGCCAATTTCAAGAGAAGTTAAGAGGAAAGAAGTACTTC
CTTGTTCTCGATGATGTATGGAACGAGGGTCGTGAGAAGTG
GCTTCATTTGGAAGAGTTGTTAATGTTGGGTCAAGGGGGAA
GCAAGGTTGTAGTGACCGACGTTCAGAGAAGACAGCAAAT
GTCATAGGGAAAAGACATTTTTATACACTGGAATGTTTGTCG
CCAGATTATTCATGGAGCTTATTTGAAATGTCGGCTTTTCAG
AAAGGGCATGAGCAGGAAAACCATGACGAACTAGTTGATAT
TGGGAAAAAGATTGTTGAAAAATGTTATAACAATCCACTTG
CTATAACGGTGGTAGGAAGTCTTCTTTATGGAGAGGAGATA
AATAAGTGGCGGTCATTTGAAATGAGTGAGTTGGCCAAAAT
TGGCAATGGGATAATAAGATTTTGTCGATATTGAAGCTCA
GTTACTACAATCTTGCAAACTCTTTGAAGAGTTGTTTTAGTT
ATTGTGCAGTATTTCCCAAGGATCATAAAATAGAGAAGGAG
ATGTTGATTGACCTTTGGATAGCACAAGGATATGTTGTGCCG
TTGGATGGAGGTCAAAGTATAGAAGATGCTGCCGAGGAACA
TTTTGTAATTTTGTTACGAAGGTGTTTCTTTCAAGATGTAGTG
AAGGATGAATACGGTGATGTTGATTCTGTTAAAATCCACGA
CTTGATGCACGATGTCGCCCAAGAAGTGGGCAGAGAGGAAA
TCTGTATAGTGAATGATAATACAAAGAACTTGGGTGATAAA
ATCCGTCATGTACATCGTGATGTCATTAGATATGCACAAAGA
GTCTCTCTGTGTAGCCATAAGATTCGTTCGTATATTGGTGGT
AAATGTGAAAAACGTTGGGTGGATACACTAATAGACAAGTG
GATGTGTCTTAGGATGTTGGACTTGTCAAATTCAGATGTTAA
AAGTTTGCCTAATTCAATAGGTAAGTTGTTGCACTTACGGTA
TCTTAACCTGTCAAATAATAGAAATCTAAAGATACTTCCTGA
TGCAATTACAAGACTGCATAACTTGCAGACACTACTTTTAGA
AGATTGCAGAAGTTTAAAGGAGTTGCCAAAAGATTTTTGCA
AATTGGTCAAACTGAGGCACTTGGATTTAAGGTTTTGTTCTG
ATTTGATTGGTATGCCATTGGGAATGGATAGGCTAACTAGTC
TTAGAGTACTGCCATTCTTTGTGGTGGGTAGGAAGGAACAA
AGTGTTGATGATGAGCTGAAAGCCCTAAAAGGCCTCACCGA
GATAAAAGGCTCCATTCGTATTAGAATCCATTCAAAGTATAG
AATAGTTGAAGGCATGAATGACACAGGAGGAGCTGGGTATT
TGAAGAGCATGAAACATCTCACGAGGGTTATTATTAGATTTG
ATGATAAAGAAGGTGGATGTGTTAACCCTGAAGCTGTGTTG
GCAACCCTAGAGCCACCTTCAAATATCAAGAGCTTATCTATA
GATAATTACGATGGTACAACAATTCCAGTATGGGGAAGAGC
AGAGATTAATTGGGCAATCTCCCTCTCACATCTTGTCGACAT
CCAGCTTTGGTGTTGTAGTAATTTGCAGGAGATGCCAGTGCT
GAGTAAACTGCCTCATTTGAAATCACTGTATCTTTTTAAGTT
TTGTAAGTTAGAGTACATGGAGAGTAGAAGCAGCAGCAGTA
GCAGTGACACAGAAGCAGCAACACCAGAATTACCAACATTC
TTCCCTTCCCTTGAAAAACTTACACTTTGGTATCTGGAAAAG
TTGAAGGGTTTTGGGAACAGGAGACCGAGTAGTTTTCCCCG
CCTCTCTAAATTGGAAATCTGGGAATGCCCAGATCTAACGTG
GTTTCCTCCTTGTCCAAGCCTTAAAACGTTGAAATTGGAAAA
AAACAATGAAGCGTTGCAAATAATAGTAAAAATAACAACAA
CAAGAGGTAAAGAAGAAAAAGAAGAAGACAAGAATGCTGG
TGTTGGAAATTCACAAGATGATGACAATGTCAAATTACGGA
AGGTGGAAATAGACAATGTGAGTTATCTCAAATCACTGCCC
ACAAATTGTCTTACTCACCTCAAAATAACTGGAATAGATTAC
AGGGAGGGGAGATTGAATCAGATTCCGTGGAGGAGGAGA
TTGAATTGGAAGTTGGGGAGGCATTTCAGAAGTGTGCATCTT
CTTTGAGAAGCCTCATCATAATCGGAAATCACGGAATAAAT
AAAGTGATGAGACTGTCTGGAAGAACAGGGTTGGAGCATTT
CACTCTGTTGGACTCACTCAAACTTTCAAATATAGAAGACCA
GGAAGATGAGGGCGAAGACAACATCATATTCTGGAAATCCT
TTCCTCAAAACCTCCGCAGTTTGGAAATTGAAAACTCTTACA
AAATGACAAGTTTGCCCATGGGGATGCAGTACTTAACCTCCC
TCCAAACCCTCTATCTACACCATTTTTATGAATTGAATTCCCT
TCCAGAATGGATAAGCAGCTTATCATCTCTTCAATACCTGCG
CATATACTACTGTCCAGCCCTGAAATCACTACCAGAAGCAAT
GCGGAACCTCACCTCCCTTCAGACACTTGGGATATCGGATTG
TCCAGACCTAGTTAAAAGATGCAGAAAACCCAACGGCAAGG
ACTATCCCAAAATTCAACACATCCCCAAAATTGACATGGATT
GA
```

TABLE 2-continued

Sequence information.

```
SEQ ID NO: 9:        MAEIGYSVCAKLIEVIGSELIKEICDTWGYKSLLEDLNKTVLTV
amino acid           RNVLIQAGVMRELTSEQQGFIADLKDVVYDADDLFDKLLTRAE
sequence of the      RKQIDGNEISEKVRRFFSSSNKIGQAYYMSRKVKEIKKQLDEIV
alpha-WOLF 25        DRHTKFGFSAEFIPVCRERGNERETRSYIDVKNILGRDKDKNDII
allele               DRLLNRNGNEACSFLTIVGAGGLGKTALAQLVFNDERVKIEFH
                     DLRYWVCVSDQDGGQFDVKEILCKILEVVTKEKVDNSSTLELV
                     QSQFQEKLRGKKYFLVLDDVWNEGREKWLHLEELLMLGQGG
                     SKVVVTARSEKTANVIGKRHFYTLECLSPDYSWSLFEMSAFQK
                     GHEQENHDELVDIGKKIVEKCYNNPLAITVVGSLLYGEEINKW
                     RSFEMSELAKIGNGDNKILSILKLSYYNLANSLKSCFSYCAVFPK
                     DHKIEKEMLIDLWIAQGYVVPLDGGQSIEDAAEEHFVILLRRCF
                     FQDVVKDEYGDVDSVKIHDLMHDVAQEVGREEICIVNDNTKN
                     LGDKIRHVHRDVIRYAQRVSLCSHKIRSYIGGKCEKRWVDTLID
                     KWMCLRMLDLSNSDVKSLPNSIGKLLHLRYLNLSNNRNLKILP
                     DAITRLHNLQTLLLEDCRSLKELPKDFCKLVKLRHLDLRFCSDL
                     IGMPLGMDRLTSLRVLPFFVVGRKEQSVDDELKALKGLTEIKG
                     SIRIRIHSKYRIVEGMNDTGGAGYLKSMKHLTRVIIRFDDKEGG
                     CVNPEAVLATLEPPSNIKSLSIDNYDGTTIPVWGRAEINWAISLS
                     HLVDIQLWCCSNLQEMPVLSKLPHLKSLYLFKFCKLEYMESRS
                     SSSSSDTEAATPELPTFFPSLEKLTLWYLEKLKGFGNRRPSSFPR
                     LSKLEIWECPDLTWFPPCPSLKTLKLEKNNEALQIIVKITTTRGK
                     EEKEEDKNAGVGNSQDDDNVKLRKVEIDNVSYLKSLPTNCLT
                     HLKITGIDYREGEIESDSVEEEIELEVGEAFQKCASSLRSLIIIGNH
                     GINKVMRLSGRTGLEHFTLLDSLKLSNIEDQEDEGEDNIIFWKSF
                     PQNLRSLEIENSYKMTSLPMGMQYLTSLQTLYLHHFYELNSLPE
                     WISSLSSLQYLRIYYCPALKSLPEAMRNLTSLQTLGISDCPDLVK
                     RCRKPNGKDYPKIQHIPKIDMD
```

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Examples

Example 1: Testing for Resistance to *Peronospora farinosa* f. Sp. *Spinaciae* in Spinach Plants The resistance to downy mildew infection was assayed as described by Irish et al. (2008; *Phytopathol.* 98: 894-900), using a differential set. Spinach plants of the invention were sown along with spinach plants from different other genotypes (see Table 3) in trays containing Scotts Redi-Earth medium, and fertilized twice a week after seedling emergence with Osmocote Peter's (13-13-13) fertilizer (Scotts). Plants were inoculated with a sporangial suspension (2.5× $10^5$/ml) of a pathogenic race of *Peronospora farinosa* f sp. *spinaciae* at the first true leaf stage. In this manner, 4 officially recognized pathogenic race were tested.

The inoculated plants were placed in a dew chamber at 18° C. with 100% relative humidity for a 24 h period, and then moved to a growth chamber at 18° C. with a 12 h photoperiod for 6 days. After 6 days, the plants were returned to the dew chamber for 24 h to induce sporulation, and they were scored for disease reaction.

Plants for this specific test were scored as resistant, intermediately resistant, or susceptible based on symptoms of chlorosis and signs of pathogen sporulation on the cotyledons and true leaves, as described by Irish et al. (2007; Plant Dis. 91: 1392-1396). Plants exhibiting no evidence of chlorosis and sporulation were in this specific test considered as resistant. Resistant plants were re-inoculated to assess whether plants initially scored as resistant had escaped infection, or whether they were truly resistant. Plants that showed only symptoms of chlorosis, or sporulation occurring only on the tips of the cotyledons were scored as intermediately resistant. Plants showing more than these symptoms of downy mildew infection were scored as being susceptible.

Table 1 shows the resistance of a plant carrying the alpha-WOLF 25 allele to each one of these pathogenic races. Table 3 shows the differential set of spinach downy mildew races and the resistance of various spinach varieties (hybrids) to each one of these pathogenic races. A susceptible reaction is scored as "+" (indicating a successful infection by the fungus, with sporulation occurring on the entire cotyledon), and resistance is depicted as "−" (absence of sporulation on the cotyledons). A weak resistance response is indicated as "(−)", which in practice means a slightly reduced level of infection (with only symptoms of chlorosis, or sporulation only occurring on the tips of the cotyledons in the differential seedling test).

TABLE 3

| Races/plants | Viroflay | Resistoflay | Califlay | Clermont | Campania | Boeing | Lion | Lazio | Whale | Polka | Pigeon | Meerkat |
|---|---|---|---|---|---|---|---|---|---|---|---|---|
| Pfs:1 | + | − | − | − | − | − | − | − | − | − | − | − |
| Pfs:2 | + | − | + | − | − | − | − | − | − | − | − | − |
| Pfs:3 | + | + | − | − | − | − | − | − | − | − | − | − |

TABLE 3-continued

| Races/plants | Viroflay | Resistoflay | Califlay | Clermont | Campania | Boeing | Lion | Lazio | Whale | Polka | Pigeon | Meerkat |
|---|---|---|---|---|---|---|---|---|---|---|---|---|
| Pfs:4  | + | + | + | − | − | − | − | − | (−) | + | − | − |
| Pfs:5  | + | + | − | + | − | − | − | − | −   | − | − | − |
| Pfs:6  | + | + | + | + | + | − | − | − | (−) | + | − | − |
| Pfs:7  | + | + | + | + | − | − | − | − | (−) | + | − | − |
| Pfs:8  | + | + | − | + | + | + | − | − | −   | − | − | − |
| Pfs:9  | + | + | − | + | + | − | − | − | −   | − | − | − |
| Pfs:10 | + | + | + | + | + | + | + | − | +   | + | − | − |
| Pfs:11 | + | + | − | + | − | − | − | + | −   | − | − | − |
| Pfs:12 | + | + | − | + | + | + | − | + | −   | − | − | − |
| Pfs:13 | + | + | + | + | (−) | − | − | + | + | (−) | − | − |
| Pfs:14 | + | + | − | + | + | + | − | + | (−) | − | + | − |
| Pfs:15 | + | + | + | − | − | − | − | − | +   | + | − | − |
| Pfs:16 | + | + | − | + | − | − | − | + | −   | − | + | + |

Example 2: Amplification of the LRR Domain-Encoding Region

The isolated genomic DNA of a spinach plant comprising the alpha-WOLF 25 allele, of which a representative sample of seed was deposited with the NCIMB under NCIMB accession number 43495 was used in polymerase chain reactions (PCR), using forward primer ACAAGTG-GATGTGTCTTAGG (SEQ ID NO: 1) and reverse primer TTCGCCCTCATCTTCCTGG (SEQ ID NO: 2). The primer pair amplifies the LRR domain-encoding region of an alpha-WOLF gene, and has been designed for selectively amplifying part of a WOLF gene, and not of other CC-NB S-LRR protein-encoding genes.

PCR conditions for amplifying the LRR domain-encoding region of an alpha-WOLF gene using primers having SEQ ID NO: 1 and SEQ ID NO: 2 were as follows, using Platinum Taq enzyme (Thermo Fisher Scientific):
  3 minutes at 95° C. (initial denaturing step)
  40 amplification cycles, each cycle consisting of: 30 seconds denaturation at 95° C., 30 seconds annealing at 60° C., and 30 seconds extension at 72° C.
  2 minutes at 72° C. (final extension step)

The isolated genomic DNA of a spinach plant of variety Viroflay comprising the beta-WOLF 0 allele was used in polymerase chain reactions (PCR), using forward primer TCACGTGGGTTGTGTTGT (SEQ ID NO: 3) and reverse primer TTCGCCCTCATCTTCCTGG (SEQ ID NO: 2). The primer pair amplifies the LRR domain-encoding region of a beta-WOLF gene, and has been designed for selectively amplifying part of a WOLF gene, and not of other CC-NBS-LRR protein-encoding genes.

PCR conditions for amplifying the LRR domain-encoding region of a beta-WOLF gene using primers having SEQ ID NO: 2 and SEQ ID NO: 3 were as follows, using Platinum Taq enzyme (Thermo Fisher Scientific):
  3 minutes at 95° C. (initial denaturing step)
  40 amplification cycles, each cycle consisting of: 30 seconds denaturation at 95° C., 50 seconds annealing at 58° C. and 50 seconds extension at 72° C.
  2 minutes at 72° C. (final extension step)

The PCR products were visualized on agarose gel (not shown), and DNA was purified from the PCR reaction. Subsequently the sequence of the PCR products was determined using methods well known in the art.

The sequence of the LRR domain of the alpha-WOLF 25 allele amplified by primers having SEQ ID NO: 1 and SEQ ID NO: 2 is provided in Table 2 under SEQ ID NO: 4.

The sequence of the LRR domain of the beta-WOLF 0 allele amplified by primers having SEQ ID NO: 2 and SEQ ID NO: 3 is provided in Table 2 under SEQ ID NO: 6.

Finally, the obtained sequences were translated into the corresponding amino acid sequence of the LRR domain having SEQ ID NO: 5 and SEQ ID NO: 7 for the alpha-WOLF 25 allele and the beta-WOLF 0, respectively (See also Table 2).

If PCR products were to be sequenced using SMRT sequencing (Pacific Biosciences), PCR primers and PCR conditions were different.

To the above-mentioned forward primers the following standard amplification sequence was added: GCAGTCGAACATGTAGCTGACTCAGGTCAC (SEQ ID NO: 13).

To the reverse primer, the following standard amplification sequence was added: TGGATCACTTGTGCAAGCAT-CACATCGTAG (SEQ ID NO: 14).

Example 3: Introducing Alpha-WOLF 25 Allele in a Plant not Carrying the Allele

A spinach plant comprising the alpha-WOLF 25 allele, of which a representative sample of seed was deposited with the NCIMB under NCIMB accession number 43495 was crossed with a plant of variety Viroflay carrying the beta-WOLF 0 allele to obtain a F1 generation. Subsequently, a F1 plant was selfed to obtain a F2 population.

Plants of the F2 population were assayed as described in Example 1 for resistance to *Peronospora farinosa* f sp. *spinaciae* Pfs:16. Approximately 75% of the plants scored completely resistant in the assay. This segregation pattern is consistent with that of a dominant inheritance.

Genomic DNA of each plant of the same F2 population was isolated and used in two different polymerase chain reactions (PCR). The first PCR reaction was done using primers for amplifying the LRR domain of an alpha-WOLF allele and the second PCR reaction was done using primers for amplifying the LRR domain of a beta-WOLF allele, both as described in Example 2.

The PCR products were visualized on agarose gel (not shown), this demonstrated that approximately 75% of the plants contained an alpha-WOLF fragment, and that the remaining approximately 25% of the plants only contained a beta-WOLF fragment. The plants containing the alpha-WOLF fragment completely correlated with the plants that scored resistant for Pfs:16. The plants only comprising the beta-WOLF fragment completely correlated with the plants that scored susceptible for Pfs:16.

DNA from the PCR reaction was purified, and subsequently the sequence of the PCR products was determined. The alpha-WOLF PCR products gave a sequence that corresponded to the sequence of SEQ ID NO: 4, the genomic sequence of the LRR domain of the alpha-WOLF 25 allele. The beta-WOLF PCR products gave a sequence that corresponded to the sequence of SEQ ID NO: 6 the genomic sequence of the LRR domain of the beta-WOLF 0 allele.

The invention is further described by the following numbered paragraphs:

1. An allele designated alpha-WOLF 25 which confers resistance to at least one *Peronospora farinosa* f. sp. *spinacea* race, wherein the protein encoded by said allele is a CC-NBS-LRR protein that comprises in its amino acid sequence: a) the motif "MAEIGYSVC" (SEQ ID NO: 10) at its N-terminus; and b) the motif "KWMCLR" (SEQ ID NO: 11); and wherein the LRR domain of the protein has in order of increased preference at least 95%, 96%, 97%, 98%, 99%, 100% sequence similarity to SEQ ID NO: 5.
2. The allele of paragraph 1 wherein the genomic DNA sequence of the LRR domain in order of increased preference has at least 95%, 96%, 97%, 98%, 99%, 100% sequence similarity to SEQ ID NO: 4.
3. The allele of paragraph 1, wherein the allele when present in a spinach plant confers complete resistance to at least *Peronospora farinosa* f. sp. *spinacea* race Pfs:8, Pfs:15 and Pfs:16, and does not confer resistance to Pfs:3.
4. A spinach plant comprising the allele of any of the paragraphs 1 to 3, of which a representative sample of seed capable of growing into a plant comprising said allele was deposited with the NCIMB under NCIMB accession number 43495.
5 The spinach plant of paragraph 4, wherein the plant is an agronomically elite plant.
6. The spinach plant of paragraph 5, wherein the agronomically elite plant is a hybrid variety or an inbred line.
7. The spinach plant of paragraph 6, further comprising a genetic determinant resulting in resistance against *Peronospora farinosa* f. sp. *spinacea* races Pfs:1 to Pfs:16.
8. Propagation material capable of developing into and/or being derived from a spinach plant as defined in any of the paragraphs 4 to 7, wherein the propagation material comprises the allele of any of the paragraphs 1 to 3 and wherein the propagation material is selected from a group consisting of a microspore, a pollen, an ovary, an ovule, an embryo, an embryo sac, an egg cell, a cutting, a root, a root tip, a hypocotyl, a cotyledon, a stem, a leaf, a flower, an anther, a seed, a meristematic cell, a protoplast, a cell, or a tissue culture thereof.
9. Cell of a spinach plant, which cell comprises the allele of any of the paragraphs 1 to 3.
10. A method of producing a hybrid spinach seed comprising crossing a first parent spinach plant with a second parent spinach plant and harvesting the resultant hybrid spinach seed, wherein said first parent spinach plant comprises the allele of any of the paragraphs 1 to 3.
11. The method of paragraph 10, wherein the first and/or second parent is a plant of an inbred line.
12. A hybrid spinach plant grown from the seed produced by the method of paragraph 10 or paragraph 11.
13. Method for identifying a spinach plant carrying the allele of paragraphs any of the paragraphs 1 to 3, comprising determining the presence of the LRR domain as defined in paragraph 1 by determining its genomic nucleotide sequence or a part thereof in the genome of a plant, wherein said sequence has in order of increased preference 95%, 96%, 97%, 98%, 99%, 100% sequence similarity to SEQ ID NO: 4.
14. The method of paragraph 13, wherein the LRR domain is determined by using a primer pair to amplify the LRR domain, wherein the forward primer is a nucleic acid molecule having the sequence of SEQ ID NO: 1.
15. The method of paragraph 13, wherein the LRR domain is determined by using a primer pair to amplify the LRR domain, wherein the reverse primer is a nucleic acid molecule having the sequence of SEQ ID NO: 2.
16. Primer pair comprising a forward primer which is a nucleic acid molecule having the sequence of SEQ ID NO: 1 and a reverse primer which is a nucleic acid molecule having the sequence of SEQ ID NO: 2.
17. A method for producing a spinach plant showing resistance to *Peronospora farinosa* f. sp. *spinaciae* comprising: (a) crossing a plant comprising the allele of paragraphs 1 or 2, with another plant; (b) optionally performing one or more rounds of selfing and/or crossing; (c) selecting after one or more rounds of selfing and/or crossing for a plant that comprises said allele of any of the paragraphs 1 to 3.
18. The method of paragraph 16, wherein the selection of a plant comprising the allele comprises determining the presence of the allele according the method of anyone of the paragraphs 13 to 15.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An agronomically elite spinach plant comprising an allele designated alpha-WOLF 25 which confers resistance to at least one *Peronospora farinosa* f sp. *spinaciae* race,
   wherein the protein encoded by the allele is a CC-NBS-LRR protein that comprises in its amino acid sequence:
   a) the motif "MAEIGYSVC" (SEQ ID NO: 10) at its N-terminus; and
   b) the motif "KWMCLR" (SEQ ID NO: 11);
   wherein the alpha-WOLF 25 allele encodes for a protein having an amino acid sequence which has at least 94% sequence identity to SEQ ID NO: 9; and
   wherein the LRR domain of the protein has at least 95%, sequence identity to SEQ ID NO: 5.

2. The spinach plant of claim 1 wherein the genomic DNA sequence of the LRR domain has at least 95%, sequence identity to SEQ ID NO: 4.

3. The spinach plant of claim 1, wherein the allele when present in a spinach plant confers complete resistance to at least *Peronospora farinosa* f. sp. *spinaciae* race Pfs:8, Pfs:15 and Pfs:16, and does not confer resistance to Pfs:3.

4. The spinach plant of claim 1, of which a representative sample of seed capable of growing into a plant comprising the allele was deposited with the NCIMB under NCIMB Accession number 43495.

5. The spinach plant of claim 1, wherein the agronomically elite plant is a hybrid variety or an inbred line.

6. The spinach plant of claim 5, further comprising a genetic determinant resulting in resistance against *Peronospora farinosa* f. sp. *spinaciae* races Pfs:1 to Pfs:16.

7. A propagation material capable of developing into and/or being derived from the spinach plant of claim 1,
   wherein the propagation material comprises the allele and
   wherein the propagation material is selected from a group consisting of a microspore, a pollen, an ovary, an ovule, an embryo, an embryo sac, an egg cell, a cutting, a root, a root tip, a hypocotyl, a cotyledon, a stem, a leaf, a flower, an anther, a seed, a meristematic cell, a protoplast, a cell, or a tissue culture thereof.

8. A cell of a spinach plant, which cell comprises the allele of the spinach plant of claim 1.

9. A method of producing a hybrid spinach seed comprising
   crossing a first parent spinach plant with a second parent spinach plant and
   harvesting the resultant hybrid spinach seed,
   wherein the first parent spinach plant comprises the allele of the spinach plant of claim 1.

10. The method of claim 9, wherein the first and/or second parent is a plant of an inbred line.

11. A hybrid spinach plant grown from the seed produced by the method of claim 9, wherein the hybrid spinach plant comprises the allele.

12. A method for identifying a spinach plant carrying the allele of the spinach plant of claim 1, comprising
   determining the presence of the LRR domain by determining its genomic nucleotide sequence or a part thereof in the genome of a plant,
   wherein the sequence has at least 95% sequence identity to SEQ ID NO: 4.

13. The method of claim 12,
   wherein the presence of the LRR domain is determined with a primer pair to amplify the LRR domain,
   wherein the forward primer is a nucleic acid molecule having the sequence of SEQ ID NO: 1.

14. The method of claim 12,
   wherein the presence of the LRR domain is determined with a primer pair to amplify the LRR domain,
   wherein the reverse primer is a nucleic acid molecule having the sequence of SEQ ID NO: 2.

15. A method for producing a spinach plant showing resistance to *Peronospora farinosa* f. sp. *spinaciae* comprising:
   (a) crossing a plant comprising the allele of the spinach plant of claim 1, with another plant;
   (b) performing one or more rounds of selfing and/or crossing;
   (c) selecting after one or more rounds of selfing and/or crossing for a plant that comprises the allele as claimed in claim 1.

16. A method for producing a spinach plant showing resistance to *Peronospora farinosa* f. sp. *spinaciae* comprising:
   (a) crossing a plant comprising an allele designated alpha-WOLF 25 which confers resistance to at least one *Peronospora farinosa* f. sp. *spinaciae* race, wherein the protein encoded by—the allele is a CC-NBS-LRR protein that comprises in its amino acid sequence:
   a) the motif "MAEIGYSVC" (SEQ ID NO: 10) at its N-terminus; and
   b) the motif "KWMCLR" (SEQ ID NO: 11);
   wherein the alpha-WOLF 25 allele encodes for a protein having an amino acid sequence which has at least 94% sequence identity to SEQ ID NO: 9;
   and wherein the LRR domain of the protein has at least 95% sequence similarity identity to SEQ ID NO: 5, with another plant;
   (b) performing one or more rounds of selfing and/or crossing;
   (c) selecting after one or more rounds of selfing and/or crossing for a plant that comprises the allele,
   wherein the selection of a plant comprising the allele comprises determining the presence of the allele according to the method of claim 12.

17. The spinach plant of claim 1, wherein the alpha-WOLF 25 allele encodes for a protein having an amino acid sequence which has at least 95% sequence identity to SEQ ID NO: 9.

18. The spinach plant of claim 1, wherein the LRR domain of the protein has at least 96% sequence identity to SEQ ID NO: 5.

19. The spinach plant of claim 1, wherein the alpha-WOLF 25 allele encodes for a protein having an amino acid sequence which has at least 96% sequence identity to SEQ ID NO: 9.

20. The spinach plant of claim 1, wherein the LRR domain of the protein has at least 97% sequence identity to SEQ ID NO: 5.

21. The spinach plant of claim 1, wherein the alpha-WOLF 25 allele encodes for a protein having an amino acid sequence which has at least 97% sequence identity to SEQ ID NO: 9.

22. The spinach plant of claim 1, wherein the LRR domain of the protein has at least 98% sequence identity to SEQ ID NO: 5.

23. The spinach plant of claim 1, wherein the alpha-WOLF 25 allele encodes for a protein having an amino acid sequence which has at least 98% sequence identity to SEQ ID NO: 9.

24. The spinach plant of claim 1, wherein the LRR domain of the protein has at least 99% sequence identity to SEQ ID NO: 5.

25. The spinach plant of claim 1, wherein the alpha-WOLF 25 allele encodes for a protein having an amino acid sequence which has at least 99% sequence identity to SEQ ID NO: 9.

26. The spinach plant of claim 1, wherein the LRR domain of the protein has 100% sequence identity to SEQ ID NO: 5.

27. The spinach plant of claim 1, wherein the alpha-WOLF 25 allele encodes for a protein having an amino acid sequence which has 100% sequence identity to SEQ ID NO: 9.

* * * * *

SEQUENCE LISTING

```
<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Forward primer LRR domain (alpha)

<400> SEQUENCE: 1
acaagtggat gtgtcttagg                                                 20
```

<210> SEQ ID NO 2
<211> LENGTH: 19
<212> TYPE: DNA
<213> ORGANISM: Artificial Sequence
<220> FEATURE:
<223> OTHER INFORMATION: Reverse primer LRR domain (alpha)

<400> SEQUENCE: 2
ttcgccctca tcttcctgg                                          19

<210> SEQ ID NO 3
<211> LENGTH: 18
<212> TYPE: DNA
<213> ORGANISM: Artificial Sequence
<220> FEATURE:
<223> OTHER INFORMATION: Forward primer LRR domain (beta)

<400> SEQUENCE: 3
tcacgtgggt tgtgttgt                                           18

<210> SEQ ID NO 4
<211> LENGTH: 1433
<212> TYPE: DNA
<213> ORGANISM: Spinacia oleracea
<220> FEATURE:
<223> OTHER INFORMATION: Amplicon of LRR domain of the alpha-WOLF 25
      allele

<400> SEQUENCE: 4
acaagtggat gtgtcttagg atgttggact tgtcaaattc agatgttaaa agtttgccta      60
attcaatagg taagttgttg cacttacggt atcttaacct gtcaaataat agaaatctaa    120
agatacttcc tgatgcaatt acaagactgc ataacttgca gacactactt ttagaagatt    180
gcagaagttt aaaggagttg ccaaaagatt tttgcaaatt ggtcaaactg aggcacttgg    240
atttaaggtt ttgttctgat ttgattggta tgccattggg aatggatagg ctaactagtc    300
ttagagtact gccattcttt gtggtgggta ggaaggaaca aagtgttgat gatgagctga    360
aagccctaaa aggcctcacc gagataaaag gctccattcg tattagaatc cattcaaagt    420
atagaatagt tgaaggcatg aatgacacag gaggagctgg gtatttgaag agcatgaaac    480
atctcacgag ggttattatt agatttgatg ataaagaagg tggatgtgtt aaccctgaag    540
ctgtgttggc aaccctagag ccaccttcaa atatcaagag cttatctata gataattacg    600
atggtacaac aattccagta tggggaagag cagagattaa ttgggcaatc tccctctcac    660
atcttgtcga catccagctt tggtgttgta gtaatttgca ggagatgcca gtgctgagta    720
aactgcctca tttgaaatca ctgtatcttt ttaagttttg taagttagag tacatggaga    780
gtagaagcag cagcagtagc agtgacacag aagcagcaac accagaatta ccaacattct    840
tcccttccct tgaaaaactt acactttggt atctggaaaa gttgaagggt tttgggaaca    900
ggagaccgag tagttttccc cgcctctcta aattggaaat ctgggaatgc ccagatctaa    960
cgtggtttcc tccttgtcca agccttaaaa cgttgaaatt ggaaaaaaac aatgaagcgt   1020
tgcaaataat agtaaaaata acaacaacaa gaggtaaaga agaaaagaa gaagacaaga    1080 atgctggtgt tggaaattca caagatgatg acaatgtcaa attacggaag gtggaaatag   1140
acaatgtgag ttatctcaaa tcactgccca caaattgtct tactcacctc aaaataactg   1200
gaatagatta cagggagggg gagattgaat cagattccgt ggaggaggag attgaattgg   1260
aagttgggga ggcatttcag aagtgtgcat cttctttgag aagcctcatc ataatcggaa   1320

```
atcacggaat aaataaagtg atgagactgt ctggaagaac agggttggag catttcactc    1380
tgttggactc actcaaactt tcaaatatag aagaccagga agatgagggc gaa           1433
```

<210> SEQ ID NO 5
<211> LENGTH: 477
<212> TYPE: PRT
<213> ORGANISM: Spinacia oleracea
<220> FEATURE:
<223> OTHER INFORMATION: amino acid sequence encoded by amplicon of LRR
      domain of alpha-WOLF 25

<400> SEQUENCE: 5

```
Lys Trp Met Cys Leu Arg Met Leu Asp Leu Ser Asn Ser Asp Val Lys
1               5                   10                  15

Ser Leu Pro Asn Ser Ile Gly Lys Leu Leu His Leu Arg Tyr Leu Asn
            20                  25                  30

Leu Ser Asn Asn Arg Asn Leu Lys Ile Leu Pro Asp Ala Ile Thr Arg
        35                  40                  45

Leu His Asn Leu Gln Thr Leu Leu Glu Asp Cys Arg Ser Leu Lys
    50                  55                  60

Glu Leu Pro Lys Asp Phe Cys Lys Leu Val Lys Leu Arg His Leu Asp
65                  70                  75                  80

Leu Arg Phe Cys Ser Asp Leu Ile Gly Met Pro Leu Gly Met Asp Arg
                85                  90                  95

Leu Thr Ser Leu Arg Val Leu Pro Phe Phe Val Val Gly Arg Lys Glu
            100                 105                 110

Gln Ser Val Asp Asp Glu Leu Lys Ala Leu Lys Gly Leu Thr Glu Ile
        115                 120                 125

Lys Gly Ser Ile Arg Ile Arg Ile His Ser Lys Tyr Arg Ile Val Glu
    130                 135                 140

Gly Met Asn Asp Thr Gly Gly Ala Gly Tyr Leu Lys Ser Met Lys His
145                 150                 155                 160

Leu Thr Arg Val Ile Ile Arg Phe Asp Asp Lys Glu Gly Gly Cys Val
                165                 170                 175

Asn Pro Glu Ala Val Leu Ala Thr Leu Glu Pro Pro Ser Asn Ile Lys
            180                 185                 190

Ser Leu Ser Ile Asp Asn Tyr Asp Gly Thr Thr Ile Pro Val Trp Gly
        195                 200                 205

Arg Ala Glu Ile Asn Trp Ala Ile Ser Leu Ser His Leu Val Asp Ile
    210                 215                 220

Gln Leu Trp Cys Cys Ser Asn Leu Gln Glu Met Pro Val Leu Ser Lys
225                 230                 235                 240

Leu Pro His Leu Lys Ser Leu Tyr Leu Phe Lys Phe Cys Lys Leu Glu
                245                 250                 255

Tyr Met Glu Ser Arg Ser Ser Ser Ser Ser Asp Thr Glu Ala Ala
            260                 265                 270

Thr Pro Glu Leu Pro Thr Phe Phe Pro Ser Leu Glu Lys Leu Thr Leu
        275                 280                 285

Trp Tyr Leu Glu Lys Leu Lys Gly Phe Gly Asn Arg Arg Pro Ser Ser
    290                 295                 300

Phe Pro Arg Leu Ser Lys Leu Glu Ile Trp Glu Cys Pro Asp Leu Thr
305                 310                 315                 320

Trp Phe Pro Pro Cys Pro Ser Leu Lys Thr Leu Lys Leu Glu Lys Asn
                325                 330                 335
```

```
Asn Glu Ala Leu Gln Ile Ile Val Lys Ile Thr Thr Thr Arg Gly Lys
                340                 345                 350

Glu Glu Lys Glu Glu Asp Lys Asn Ala Gly Val Gly Asn Ser Gln Asp
            355                 360                 365

Asp Asp Asn Val Lys Leu Arg Lys Val Glu Ile Asp Asn Val Ser Tyr
        370                 375                 380

Leu Lys Ser Leu Pro Thr Asn Cys Leu Thr His Leu Lys Ile Thr Gly
385                 390                 395                 400

Ile Asp Tyr Arg Glu Gly Glu Ile Glu Ser Asp Ser Val Glu Glu Glu
                405                 410                 415

Ile Glu Leu Glu Val Gly Glu Ala Phe Gln Lys Cys Ala Ser Ser Leu
            420                 425                 430

Arg Ser Leu Ile Ile Ile Gly Asn His Gly Ile Asn Lys Val Met Arg
        435                 440                 445

Leu Ser Gly Arg Thr Gly Leu Glu His Phe Thr Leu Leu Asp Ser Leu
450                 455                 460

Lys Leu Ser Asn Ile Glu Asp Gln Glu Asp Glu Gly Glu
465                 470                 475
```

<210> SEQ ID NO 6
<211> LENGTH: 1597
<212> TYPE: DNA
<213> ORGANISM: Spinacia oleracea
<220> FEATURE:
<223> OTHER INFORMATION: Amplicon of LRR domain of the beta-WOLF 0
      allele

<400> SEQUENCE: 6

```
tcacgtgggt tgtgttgtcg atagagatcc agaaatagtc tttttatgta gcaataagat      60
tcgttcgtat attagcggtc gctgcataaa gaatccggtg gattcacaaa tagacaactg     120
gatgtgcctt agggtgttgg acttgtcaga ttcatgtgtt aaagatttgt ctgattcaat     180
aggtaagctg ctgcacttaa ggtatcttaa cctctcttct aatataaagt tggagataat     240
ccctgatgca attacaagac tgcataactt gcagacacta cttttagaag attgcagaag     300
tttaaaggag ttgccaaaag attttttgcaa attggtcaaa ctgaggcact tggaattaca     360
gggttgtcat gatttgattg gtatgtcatt tggaatggat aagctaacta gtcttagaat     420
actaccaaac attgtggtgg gtaggaagga acaaagtgtt gatgatgagc tgaaagccct     480
aaaaggcctc accgagataa aaggctccat tgatatcaca atctattcaa aatatagaag     540
agttgaaggc atgaatggca caggaggagg agctgggtat ttgaagagca tgaaacatct     600
cacgggggtt aatattacat ttgatgaagg tggatgtgtt aaccctgaag ctgtgtattt     660
gaagagcatg aaacatctca cgagggttat tattatattt gattataaag gtggatgtgt     720
taaccctgaa gctgtgttgg caaccctaga gccaccttca aatatcaaga ggttagagat     780
gtggcattac agtggtacaa caattccagt atggggaaga gcagagatta ttgggcaat     840
ctccctctca catcttgtcg acatcacgct tgaagattgt tacaatttgc aggagatgcc     900
agtgctgagt aaactgcctc atttgaaatc actggaactt acagagttgg ataacttaga     960
gtacatggag agtagaagca gcagcagtag cagtgacaca gaagcagcaa caccagaatt    1020
accaacattc ttcccttccc ttgaaaaact tacactttgg cgtctggaca agttgaaggg    1080
tttggggaac aggagatcga gtagttttcc ccgcctctct aaattggaaa tctggaaatg    1140
tccagatcta acgtcatttc cttccttgtcc aagccttgaa gagttggaat tgaaagaaaa    1200
caatgaagcg ttgcaaataa tagtaaaaat aacaacaaca agaggtaaag aagaaaaaga    1260
```

```
agaagacaag aatgctggtg ttggaaattc acaagatgat gacaatgtca aattatggaa    1320
ggtggaaata gacaatctgg gttatctcaa atcactgccc acaaattgtc tgactcacct    1380
cgaccttaca ataagtgatt ccaaggaggg ggagggtgaa tgggaagttg gggatgcatt    1440
tcagaagtgt gtatcttctt tgagaagcct caccataatc ggaaatcacg gaataaataa    1500
agtgaagaga ctgtctggaa aacagggtt ggagcatttc actctgttgg aatcactcaa    1560
actttcagat atagaagacc aggaagatga gggcgaa                             1597
```

<210> SEQ ID NO 7
<211> LENGTH: 532
<212> TYPE: PRT
<213> ORGANISM: Spinacia oleracea
<220> FEATURE:
<223> OTHER INFORMATION: amino acid sequence encoded by amplicon of LRR
      domain Beta Wolf 0 (Viroflay)

<400> SEQUENCE: 7

```
His Val Gly Cys Val Val Asp Arg Asp Pro Glu Ile Val Phe Leu Cys
1               5                   10                  15

Ser Asn Lys Ile Arg Ser Tyr Ile Ser Gly Arg Cys Ile Lys Asn Pro
            20                  25                  30

Val Asp Ser Gln Ile Asp Asn Trp Met Cys Leu Arg Val Leu Asp Leu
        35                  40                  45

Ser Asp Ser Cys Val Lys Asp Leu Ser Asp Ser Ile Gly Lys Leu Leu
    50                  55                  60

His Leu Arg Tyr Leu Asn Leu Ser Ser Asn Ile Lys Leu Glu Ile Ile
65                  70                  75                  80

Pro Asp Ala Ile Thr Arg Leu His Asn Leu Gln Thr Leu Leu Leu Glu
                85                  90                  95

Asp Cys Arg Ser Leu Lys Glu Leu Pro Lys Asp Phe Cys Lys Leu Val
            100                 105                 110

Lys Leu Arg His Leu Glu Leu Gln Gly Cys His Asp Leu Ile Gly Met
        115                 120                 125

Ser Phe Gly Met Asp Lys Leu Thr Ser Leu Arg Ile Leu Pro Asn Ile
    130                 135                 140

Val Val Gly Arg Lys Glu Gln Ser Val Asp Asp Glu Leu Lys Ala Leu
145                 150                 155                 160

Lys Gly Leu Thr Glu Ile Lys Gly Ser Ile Asp Ile Thr Ile Tyr Ser
                165                 170                 175

Lys Tyr Arg Arg Val Glu Gly Met Asn Gly Thr Gly Gly Ala Gly
            180                 185                 190

Tyr Leu Lys Ser Met Lys His Leu Thr Gly Val Asn Ile Thr Phe Asp
    195                 200                 205

Glu Gly Gly Cys Val Asn Pro Glu Ala Val Tyr Leu Lys Ser Met Lys
210                 215                 220

His Leu Thr Arg Val Ile Ile Phe Asp Tyr Lys Gly Gly Cys Val
225                 230                 235                 240

Asn Pro Glu Ala Val Leu Ala Thr Leu Glu Pro Ser Asn Ile Lys
                245                 250                 255

Arg Leu Glu Met Trp His Tyr Ser Gly Thr Thr Ile Pro Val Trp Gly
            260                 265                 270

Arg Ala Glu Ile Asn Trp Ala Ile Ser Leu Ser His Leu Val Asp Ile
        275                 280                 285

Thr Leu Glu Asp Cys Tyr Asn Leu Gln Glu Met Pro Val Leu Ser Lys
```

```
                290                 295                 300

Leu Pro His Leu Lys Ser Leu Glu Leu Thr Glu Leu Asp Asn Leu Glu
305                 310                 315                 320

Tyr Met Glu Ser Arg Ser Ser Ser Ser Ser Asp Thr Glu Ala Ala
                325                 330                 335

Thr Pro Glu Leu Pro Thr Phe Phe Pro Ser Leu Glu Lys Leu Thr Leu
                340                 345                 350

Trp Arg Leu Asp Lys Leu Lys Gly Phe Gly Asn Arg Arg Ser Ser Ser
                355                 360                 365

Phe Pro Arg Leu Ser Lys Leu Glu Ile Trp Lys Cys Pro Asp Leu Thr
370                 375                 380

Ser Phe Pro Ser Cys Pro Ser Leu Glu Glu Leu Glu Leu Lys Glu Asn
385                 390                 395                 400

Asn Glu Ala Leu Gln Ile Ile Val Lys Ile Thr Thr Thr Arg Gly Lys
                405                 410                 415

Glu Glu Lys Glu Glu Asp Lys Asn Ala Gly Val Gly Asn Ser Gln Asp
                420                 425                 430

Asp Asp Asn Val Lys Leu Trp Lys Val Glu Ile Asp Asn Leu Gly Tyr
                435                 440                 445

Leu Lys Ser Leu Pro Thr Asn Cys Leu Thr His Leu Asp Leu Thr Ile
                450                 455                 460

Ser Asp Ser Lys Glu Gly Glu Gly Glu Trp Glu Val Gly Asp Ala Phe
465                 470                 475                 480

Gln Lys Cys Val Ser Ser Leu Arg Ser Leu Thr Ile Ile Gly Asn His
                485                 490                 495

Gly Ile Asn Lys Val Lys Arg Leu Ser Gly Arg Thr Gly Leu Glu His
                500                 505                 510

Phe Thr Leu Leu Glu Ser Leu Lys Leu Ser Asp Ile Glu Asp Gln Glu
                515                 520                 525

Asp Glu Gly Glu
    530

<210> SEQ ID NO 8
<211> LENGTH: 3486
<212> TYPE: DNA
<213> ORGANISM: Spinacia oleracea
<220> FEATURE:
<223> OTHER INFORMATION: coding sequence of the alpha-WOLF 25 allele

<400> SEQUENCE: 8
atggccgaaa tcggatactc ggtttgtgcg aaactcatcg aagtgattgg cagtgagctg      60
atcaaagaga tttgtgacac atggggttac aaatctcttc ttgaggacct caacaaaact     120
gtattgacgg tcaggaacgt tctcattcaa gccggggtga tgcgggagct tactagtgaa     180
caacaaggtt tcattgcaga ccttaaagat gttgtttatg atgctgatga cttgttcgac     240
aagttactca ctcgtgctga gcgaaaacag attgatggaa acgaaatctc tgaaaaggta     300
cgtcgtttct tttcctctag taacaagatc ggtcaagctt actacatgtc tcgtaaggtt     360
aaggaaatta agaagcagtt ggatgaaatt gttgataggc atacaaaatt tgggtttagt     420
gctgagttta tacctgtttg tagggaaagg gggaacgaga gggaaacacg ttcatatata     480
gatgtcaaga atattcttgg gagggataaa gataagaatg atatcattga taggttgctt     540
aatcgtaatg gtaatgaagc ttgtagtttc ctgaccatag tgggagcggg aggattggga     600
aaaactgctc ttgcacaact tgtgttcaat gatgaaaggg tcaaaattga gtttcatgat     660
```

```
ttgaggtatt gggtttgtgt ctctgatcaa gatgggggcc aatttgatgt gaaagaaatc    720
ctttgtaaga ttttagaggt ggttactaag gagaaagttg ataatagttc cacattggaa    780
ttggtgcaaa gccaatttca agagaagtta agaggaaaga agtacttcct tgttctcgat    840
gatgtatgga acgagggtcg tgagaagtgg cttcatttgg aagagttgtt aatgttgggt    900 caaggggggaa gcaaggttgt agtgaccgca cgttcagaga agacagcaaa tgtcataggg    960
aaaagacatt tttatacact ggaatgtttg tcgccagatt attcatggag cttatttgaa   1020
atgtcggctt ttcagaaagg gcatgagcag gaaaaccatg acgaactagt tgatattggg   1080
aaaaagattg ttgaaaaatg ttataacaat ccacttgcta taacggtggt aggaagtctt   1140
ctttatggag aggagataaa taagtggcgg tcatttgaaa tgagtgagtt ggccaaaatt   1200
ggcaatgggg ataataagat tttgtcgata ttgaagctca gttactacaa tcttgcaaac   1260
tctttgaaga gttgttttag ttattgtgca gtatttccca aggatcataa aatagagaag   1320
gagatgttga ttgacctttg gatagcacaa ggatatgttg tgccgttgga tggaggtcaa   1380
agtatagaag atgctgccga ggaacatttt gtaattttgt tacgaaggtg tttctttcaa   1440
gatgtagtga aggatgaata cggtgatgtt gattctgtta aaatccacga cttgatgcac   1500
gatgtcgccc aagaagtggg cagagaggaa atctgtatag tgaatgataa tacaaagaac   1560
ttgggtgata aaatccgtca tgtacatcgt gatgtcatta gatatgcaca aagagtctct   1620
ctgtgtagcc ataagattcg ttcgtatatt ggtggtaaat gtgaaaaacg ttgggtggat   1680
acactaatag acaagtggat gtgtcttagg atgttggact tgtcaaattc agatgttaaa   1740
agtttgccta attcaatagg taagttgttg cacttacggt atcttaacct gtcaaataat   1800
agaaatctaa agatacttcc tgatgcaatt acaagactgc ataacttgca gacactactt   1860
ttagaagatt gcagaagttt aaaggagttg ccaaaagatt tttgcaaatt ggtcaaactg   1920
aggcacttgg atttaaggtt ttgttctgat ttgattggta tgccattggg aatggatagg   1980
ctaactagtc ttagagtact gccattcttt gtggtgggta ggaaggaaca aagtgttgat   2040
gatgagctga aagccctaaa aggcctcacc gagataaaag gctccattcg tattagaatc   2100
cattcaaagt atagaatagt tgaaggcatg aatgacacag gaggagctgg gtatttgaag   2160
agcatgaaac atctcacgag ggttattatt agatttgatg ataaagaagg tggatgtgtt   2220
aaccctgaag ctgtgttggc aaccctagag ccaccttcaa atatcaagag cttatctata   2280
gataattacg atggtacaac aattccagta tggggaagag cagagattaa ttgggcaatc   2340
tccctctcac atcttgtcga catccagctt tggtgttgta gtaatttgca ggagatgcca   2400
gtgctgagta aactgcctca tttgaaatca ctgtatcttt ttaagttttg taagttagag   2460
tacatggaga gtagaagcag cagcagtagc agtgacacag aagcagcaac accagaatta   2520
ccaacattct tcccttccct tgaaaaactt acactttggt atctggaaaa gttgaagggt   2580
tttgggaaca ggagaccgag tagttttccc cgcctctcta aattggaaat ctgggaatgc   2640
ccagatctaa cgtggtttcc tccttgtcca agccttaaaa cgttgaaatt ggaaaaaaac   2700
aatgaagcgt tgcaaataat agtaaaaata acaacaacaa gaggtaaaga agaaaaagaa   2760
gaagacaaga atgctggtgt tggaaattca caagatgatg acaatgtcaa attacggaag   2820
gtggaaatag acaatgtgag ttatctcaaa tcactgccca caaattgtct tactcacctc   2880
aaaataactg gaatagatta cagggagggg gagattgaat cagattccgt ggaggaggag   2940
attgaattgg aagttgggga ggcatttcag aagtgtgcat cttctttgag aagcctcatc   3000
ataatcggaa atcacggaat aaataaagtg atgagactgt ctggaagaac agggttggag   3060
```

-continued

```
catttcactc tgttggactc actcaaactt tcaaatatag aagaccagga agatgagggc    3120
gaagacaaca tcatattctg gaaatccttt cctcaaaacc tccgcagttt ggaaattgaa    3180
aactcttaca aaatgacaag tttgcccatg gggatgcagt acttaacctc cctccaaacc    3240
ctctatctac accatttta tgaattgaat tcccttccag aatggataag cagcttatca     3300
tctcttcaat acctgcgcat atactactgt ccagccctga atcactacc agaagcaatg     3360 cggaacctca cctcccttca gacacttggg atatcggatt gtccagacct agttaaaaga    3420
tgcagaaaac ccaacggcaa ggactatccc aaaattcaac acatcccaa aattgacatg     3480 gattga                                                              3486
```

<210> SEQ ID NO 9
<211> LENGTH: 1161
<212> TYPE: PRT
<213> ORGANISM: Spinacia oleracea
<220> FEATURE:
<223> OTHER INFORMATION: amino acid sequence of the alpha-WOLF 25 allele

<400> SEQUENCE: 9

```
Met Ala Glu Ile Gly Tyr Ser Val Cys Ala Lys Leu Ile Glu Val Ile
1               5                   10                  15

Gly Ser Glu Leu Ile Lys Glu Ile Cys Asp Thr Trp Gly Tyr Lys Ser
            20                  25                  30

Leu Leu Glu Asp Leu Asn Lys Thr Val Leu Thr Val Arg Asn Val Leu
        35                  40                  45

Ile Gln Ala Gly Val Met Arg Glu Leu Thr Ser Glu Gln Gln Gly Phe
    50                  55                  60

Ile Ala Asp Leu Lys Asp Val Val Tyr Asp Ala Asp Leu Phe Asp
65                  70                  75                  80

Lys Leu Leu Thr Arg Ala Glu Arg Lys Gln Ile Asp Gly Asn Glu Ile
                85                  90                  95

Ser Glu Lys Val Arg Arg Phe Phe Ser Ser Ser Asn Lys Ile Gly Gln
            100                 105                 110

Ala Tyr Tyr Met Ser Arg Lys Val Lys Glu Ile Lys Lys Gln Leu Asp
        115                 120                 125

Glu Ile Val Asp Arg His Thr Lys Phe Gly Phe Ser Ala Glu Phe Ile
    130                 135                 140

Pro Val Cys Arg Glu Arg Gly Asn Glu Arg Glu Thr Arg Ser Tyr Ile
145                 150                 155                 160

Asp Val Lys Asn Ile Leu Gly Arg Asp Lys Asp Lys Asn Asp Ile Ile
                165                 170                 175

Asp Arg Leu Leu Asn Arg Asn Gly Asn Glu Ala Cys Ser Phe Leu Thr
            180                 185                 190

Ile Val Gly Ala Gly Gly Leu Gly Lys Thr Ala Leu Ala Gln Leu Val
        195                 200                 205

Phe Asn Asp Glu Arg Val Lys Ile Glu Phe His Asp Leu Arg Tyr Trp
    210                 215                 220

Val Cys Val Ser Asp Gln Asp Gly Gly Gln Phe Asp Val Lys Glu Ile
225                 230                 235                 240

Leu Cys Lys Ile Leu Glu Val Val Thr Lys Glu Lys Val Asp Asn Ser
                245                 250                 255

Ser Thr Leu Glu Leu Val Gln Ser Gln Phe Gln Glu Lys Leu Arg Gly
            260                 265                 270

Lys Lys Tyr Phe Leu Val Leu Asp Asp Val Trp Asn Glu Gly Arg Glu
```

```
            275                 280                 285
Lys Trp Leu His Leu Glu Glu Leu Leu Met Leu Gly Gln Gly Gly Ser
290                 295                 300
Lys Val Val Thr Ala Arg Ser Glu Lys Thr Ala Asn Val Ile Gly
305                 310                 315                 320
Lys Arg His Phe Tyr Thr Leu Glu Cys Leu Ser Pro Asp Tyr Ser Trp
                    325                 330                 335
Ser Leu Phe Glu Met Ser Ala Phe Gln Lys Gly His Glu Gln Glu Asn
                340                 345                 350
His Asp Glu Leu Val Asp Ile Gly Lys Lys Ile Val Glu Lys Cys Tyr
                355                 360                 365
Asn Asn Pro Leu Ala Ile Thr Val Val Gly Ser Leu Leu Tyr Gly Glu
370                 375                 380
Glu Ile Asn Lys Trp Arg Ser Phe Glu Met Ser Glu Leu Ala Lys Ile
385                 390                 395                 400
Gly Asn Gly Asp Asn Lys Ile Leu Ser Ile Leu Lys Leu Ser Tyr Tyr
                    405                 410                 415
Asn Leu Ala Asn Ser Leu Lys Ser Cys Phe Ser Tyr Cys Ala Val Phe
                420                 425                 430
Pro Lys Asp His Lys Ile Glu Lys Glu Met Leu Ile Asp Leu Trp Ile
            435                 440                 445
Ala Gln Gly Tyr Val Val Pro Leu Asp Gly Gly Gln Ser Ile Glu Asp
450                 455                 460
Ala Ala Glu Glu His Phe Val Ile Leu Leu Arg Arg Cys Phe Phe Gln
465                 470                 475                 480
Asp Val Val Lys Asp Glu Tyr Gly Asp Val Asp Ser Val Lys Ile His
                    485                 490                 495
Asp Leu Met His Asp Val Ala Gln Glu Val Gly Arg Glu Glu Ile Cys
                500                 505                 510
Ile Val Asn Asp Asn Thr Lys Asn Leu Gly Asp Lys Ile Arg His Val
            515                 520                 525
His Arg Asp Val Ile Arg Tyr Ala Gln Arg Val Ser Leu Cys Ser His
530                 535                 540
Lys Ile Arg Ser Tyr Ile Gly Gly Lys Cys Glu Lys Arg Trp Val Asp
545                 550                 555                 560
Thr Leu Ile Asp Lys Trp Met Cys Leu Arg Met Leu Asp Leu Ser Asn
                    565                 570                 575
Ser Asp Val Lys Ser Leu Pro Asn Ser Ile Gly Lys Leu Leu His Leu
                580                 585                 590
Arg Tyr Leu Asn Leu Ser Asn Asn Arg Asn Leu Lys Ile Leu Pro Asp
            595                 600                 605
Ala Ile Thr Arg Leu His Asn Leu Gln Thr Leu Leu Leu Glu Asp Cys
610                 615                 620
Arg Ser Leu Lys Glu Leu Pro Lys Asp Phe Cys Lys Leu Val Lys Leu
625                 630                 635                 640
Arg His Leu Asp Leu Arg Phe Cys Ser Asp Leu Ile Gly Met Pro Leu
                    645                 650                 655
Gly Met Asp Arg Leu Thr Ser Leu Arg Val Leu Pro Phe Phe Val Val
                660                 665                 670
Gly Arg Lys Glu Gln Ser Val Asp Asp Glu Leu Lys Ala Leu Lys Gly
            675                 680                 685
Leu Thr Glu Ile Lys Gly Ser Ile Arg Ile Arg Ile His Ser Lys Tyr
690                 695                 700
```

-continued

Arg Ile Val Glu Gly Met Asn Asp Thr Gly Ala Gly Tyr Leu Lys
705                 710                 715                 720

Ser Met Lys His Leu Thr Arg Val Ile Ile Arg Phe Asp Asp Lys Glu
            725                 730                 735

Gly Gly Cys Val Asn Pro Glu Ala Val Leu Ala Thr Leu Glu Pro Pro
        740                 745                 750

Ser Asn Ile Lys Ser Leu Ser Ile Asp Asn Tyr Asp Gly Thr Thr Ile
    755                 760                 765

Pro Val Trp Gly Arg Ala Glu Ile Asn Trp Ala Ile Ser Leu Ser His
770                 775                 780

Leu Val Asp Ile Gln Leu Trp Cys Cys Ser Asn Leu Gln Glu Met Pro
785                 790                 795                 800

Val Leu Ser Lys Leu Pro His Leu Lys Ser Leu Tyr Leu Phe Lys Phe
            805                 810                 815

Cys Lys Leu Glu Tyr Met Glu Ser Arg Ser Ser Ser Ser Ser Ser Asp
        820                 825                 830

Thr Glu Ala Ala Thr Pro Glu Leu Pro Thr Phe Phe Pro Ser Leu Glu
    835                 840                 845

Lys Leu Thr Leu Trp Tyr Leu Glu Lys Leu Lys Gly Phe Gly Asn Arg
850                 855                 860

Arg Pro Ser Ser Phe Pro Arg Leu Ser Lys Leu Glu Ile Trp Glu Cys
865                 870                 875                 880

Pro Asp Leu Thr Trp Phe Pro Pro Cys Pro Ser Leu Lys Thr Leu Lys
            885                 890                 895

Leu Glu Lys Asn Asn Glu Ala Leu Gln Ile Ile Val Lys Ile Thr Thr
        900                 905                 910

Thr Arg Gly Lys Glu Lys Glu Glu Asp Lys Asn Ala Gly Val Gly
    915                 920                 925

Asn Ser Gln Asp Asp Asn Val Lys Leu Arg Lys Val Glu Ile Asp
    930                 935                 940

Asn Val Ser Tyr Leu Lys Ser Leu Pro Thr Asn Cys Leu Thr His Leu
945                 950                 955                 960

Lys Ile Thr Gly Ile Asp Tyr Arg Glu Gly Glu Ile Glu Ser Asp Ser
            965                 970                 975

Val Glu Glu Glu Ile Glu Leu Glu Val Gly Glu Ala Phe Gln Lys Cys
        980                 985                 990

Ala Ser Ser Leu Arg Ser Leu Ile Ile Ile Gly Asn His Gly Ile Asn
    995                 1000                1005

Lys Val Met Arg Leu Ser Gly Arg Thr Gly Leu Glu His Phe Thr Leu
    1010                1015                1020

Leu Asp Ser Leu Lys Leu Ser Asn Ile Glu Asp Gln Glu Asp Glu Gly
1025                1030                1035                1040

Glu Asp Asn Ile Ile Phe Trp Lys Ser Phe Pro Gln Asn Leu Arg Ser
        1045                1050                1055

Leu Glu Ile Glu Asn Ser Tyr Lys Met Thr Ser Leu Pro Met Gly Met
    1060                1065                1070

Gln Tyr Leu Thr Ser Leu Gln Thr Leu Tyr Leu His His Phe Tyr Glu
    1075                1080                1085

Leu Asn Ser Leu Pro Glu Trp Ile Ser Ser Leu Ser Ser Leu Gln Tyr
    1090                1095                1100

Leu Arg Ile Tyr Tyr Cys Pro Ala Leu Lys Ser Leu Pro Glu Ala Met
1105                1110                1115                1120

```
Arg Asn Leu Thr Ser Leu Gln Thr Leu Gly Ile Ser Asp Cys Pro Asp
            1125                1130                1135

Leu Val Lys Arg Cys Arg Lys Pro Asn Gly Lys Asp Tyr Pro Lys Ile
        1140                1145                1150

Gln His Ile Pro Lys Ile Asp Met Asp
        1155                1160

<210> SEQ ID NO 10
<211> LENGTH: 9
<212> TYPE: PRT
<213> ORGANISM: Spinacia oleracea
<220> FEATURE:
<223> OTHER INFORMATION: N-terminal motif CC-NBS-LRR protein

<400> SEQUENCE: 10

Met Ala Glu Ile Gly Tyr Ser Val Cys
1               5

<210> SEQ ID NO 11
<211> LENGTH: 6
<212> TYPE: PRT
<213> ORGANISM: Spinacia oleracea
<220> FEATURE:
<223> OTHER INFORMATION: Motif CC-NBS-LRR protein

<400> SEQUENCE: 11

Lys Trp Met Cys Leu Arg
1               5

<210> SEQ ID NO 12
<211> LENGTH: 9
<212> TYPE: PRT
<213> ORGANISM: Spinacia oleracea
<220> FEATURE:
<223> OTHER INFORMATION: motif alpha-WOLF 25 allele

<400> SEQUENCE: 12

Asp Gln Glu Asp Glu Gly Glu Asp Asn
1               5

<210> SEQ ID NO 13
<211> LENGTH: 30
<212> TYPE: DNA
<213> ORGANISM: Spinacia oleracea
<220> FEATURE:
<223> OTHER INFORMATION: Forward primer standard amplification sequence

<400> SEQUENCE: 13
gcagtcgaac atgtagctga ctcaggtcac                                      30

<210> SEQ ID NO 14
<211> LENGTH: 30
<212> TYPE: DNA
<213> ORGANISM: Spinacia oleracea
<220> FEATURE:
<223> OTHER INFORMATION: Reverse primer standard amplification sequence

<400> SEQUENCE: 14
tggatcactt gtgcaagcat cacatcgtag                                      30

<210> SEQ ID NO 15
<211> LENGTH: 8
<212> TYPE: PRT
<213> ORGANISM: Spinacia oleracea
<220> FEATURE:
<223> OTHER INFORMATION: motif alpha-WOLF 25 allele
```

```
<400> SEQUENCE: 15

His Val Gly Cys Val Val Asp Arg
1               5
```

UNITED STATES PATENT AND TRADEMARK OFFICE
CERTIFICATE OF CORRECTION

PATENT NO. : 11,603,538 B2
APPLICATION NO. : 16/722582
DATED : March 14, 2023
INVENTOR(S) : Raoul Jacobus Johannes Maria Frijters et al.

It is certified that error appears in the above-identified patent and that said Letters Patent is hereby corrected as shown below:

On the Title Page

Item (57) The Abstract should read as:
(57) ABSTRACT
The present invention relates to an allele designated alpha-WOLF 25 which confers resistance to at least one Peronospora farinosa f. sp. spinacea race, wherein the protein encoded by said allele is a CC-NBS-LRR protein that comprises in its amino acid sequence: a) the motif "MAEIGYSVC" at its N-terminus; and b) the motif "KWMCLR"; and wherein the LRR domain of the protein has in order of increased preference at least 95%, 96%, 97%, 98%, 99%, 100% sequence similarity to SEQ ID NO: 5. The allele when present in a spinach plant confers complete resistance to at least Peronospora farinosa f sp. spinacea race Pfs:8, Pfs:15 and Pfs:16, and does not confer resistance to Pfs:3.

In the Claims

Claim 15 should read as:
15. A method for producing a spinach plant showing resistance to Peronospora farinosa f. sp. spinaciae comprising: (a) crossing a plant comprising the allele of the spinach plant of claim 1, with another plant; (b) performing one or more rounds of selfing and/or crossing; (c) selecting after one or more rounds of selfing and/or crossing for a plant that comprises the allele.

Claim 16 should read as:
16. A method for producing a spinach plant showing resistance to Peronospora farinosa f. sp. spinaciae comprising: (a) crossing a plant comprising an allele designated alpha-WOLF 25 which confers resistance to at least one Peronospora farinosa f. sp. spinaciae race, wherein the protein encoded by the allele is a CC-NBS-LRR protein that comprises in its amino acid sequence: a) the motif "MAEIGYSVC" (SEQ ID NO: 10) at its N-terminus; and b) the motif "KWMCLR" (SEQ ID NO: 11); wherein the alpha-WOLF 25 allele encodes for a protein having an amino acid sequence which has at least 94% sequence identity to SEQ ID NO: 9; and wherein the LRR domain of the protein has at least 95% sequence identity to SEQ ID NO: 5, with another plant; (b) performing one or more rounds of selfing and/or crossing; (c) selecting after one or more rounds of selfing and/or Signed and Sealed this
Nineteenth Day of March, 2024

Katherine Kelly Vidal
*Director of the United States Patent and Trademark Office*